(12) United States Patent
Fritz et al.

(10) Patent No.: US 6,970,245 B2
(45) Date of Patent: Nov. 29, 2005

(54) OPTICAL ALIGNMENT DETECTION SYSTEM

(75) Inventors: Bernard S. Fritz, Eagan, MN (US); Aravind Padmanabhan, Plymouth, MN (US); Peter Reutiman, Crystal, MN (US)

(73) Assignee: Honeywell International Inc., Morristown, NJ (US)

(*) Notice: Subject to any disclaimer, the term of this patent is extended or adjusted under 35 U.S.C. 154(b) by 477 days.

(21) Appl. No.: 10/225,325

(22) Filed: Aug. 21, 2002

(65) Prior Publication Data

US 2003/0058445 A1 Mar. 27, 2003

Related U.S. Application Data

(63) Continuation-in-part of application No. 09/630,927, filed on Aug. 2, 2000, now Pat. No. 6,549,275.

(51) Int. Cl.⁷ .............................. G01B 11/00
(52) U.S. Cl. .................... 356/400; 356/401
(58) Field of Search .................. 356/400–401

(56) References Cited

U.S. PATENT DOCUMENTS

| | | | |
|---|---|---|---|
| 3,822,095 A | 7/1974 | Hirschfeld | |
| 3,928,094 A | * 12/1975 | Angell | 356/400 |
| 4,478,076 A | 10/1984 | Bohrer | |
| 4,478,077 A | 10/1984 | Boher | |
| 4,501,144 A | 2/1985 | Higashi et al. | |
| 4,599,000 A | * 7/1986 | Yamada | 356/401 |
| 4,651,564 A | 3/1987 | Johnson et al. | |
| 4,683,159 A | 7/1987 | Bohrer et al. | |
| 4,695,034 A | 9/1987 | Shimizu et al. | |
| 4,704,033 A | 11/1987 | Fay et al. | |
| 4,818,263 A | 4/1989 | Mitch | |
| 4,911,616 A | 3/1990 | Laumann, Jr. | |
| 4,932,989 A | 6/1990 | Presby | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,441,597 A | 8/1995 | Bonne et al. | |

(Continued)

FOREIGN PATENT DOCUMENTS

DE 10122321 4/2002

(Continued)

OTHER PUBLICATIONS http://www.micronics.net/tsensor.htm, pp. 1-4, downloaded Jun. 14, 2000.

(Continued)

*Primary Examiner*—Layla G. Lauchman
(74) *Attorney, Agent, or Firm*—Kris T. Fredrick

(57) ABSTRACT

An optical alignment detection system for detecting the alignment of a first object relative to a second object is provided. One or more light sources and one or more light detectors, either or both of which are secured relative to the second object, are used to detect the position of one or more light scattering elements on the first object.

25 Claims, 19 Drawing Sheets

U.S. PATENT DOCUMENTS

| | | |
|---|---|---|
| 5,452,878 A | 9/1995 | Gravesen et al. |
| 5,570,193 A | 10/1996 | Landa et al. |
| 5,616,501 A | 4/1997 | Rodriguez |
| 5,683,159 A | 11/1997 | Johnson |
| 5,716,852 A | 2/1998 | Yager et al. |
| 5,717,631 A | 2/1998 | Carley et al. |
| 5,726,751 A | 3/1998 | Altendorf et al. |
| 5,757,476 A | 5/1998 | Nakamoto et al. |
| 5,793,485 A | 8/1998 | Gourley |
| 5,799,030 A | 8/1998 | Brenner |
| 5,822,170 A | 10/1998 | Cabuz et al. |
| 5,836,750 A | 11/1998 | Cabuz |
| 5,839,807 A | 11/1998 | Perlo |
| 5,863,502 A | 1/1999 | Southgate et al. |
| 5,893,722 A | 4/1999 | Hibbs-Brenner et al. |
| 5,901,939 A | 5/1999 | Cabuz et al. |
| 5,922,210 A | 7/1999 | Brody et al. |
| 5,932,100 A | 8/1999 | Yager et al. |
| 5,948,684 A | 9/1999 | Weigl et al. |
| 5,970,315 A | 10/1999 | Carley et al. |
| 5,971,158 A | 10/1999 | Yager et al. |
| 5,972,710 A | 10/1999 | Weigl et al. |
| 5,974,867 A | 11/1999 | Forster et al. |
| 6,007,775 A | 12/1999 | Yager |
| 6,032,689 A | 3/2000 | Tsai et al. |
| 6,054,335 A | 4/2000 | Sun et al. |
| 6,082,185 A | 7/2000 | Saaski |
| 6,091,197 A | 7/2000 | Sun et al. |
| 6,091,537 A | 7/2000 | Sun et al. |
| 6,094,293 A | 7/2000 | Yokoyama et al. |
| 6,097,485 A | 8/2000 | Lievan |
| 6,097,859 A | 8/2000 | Solgaard et al. |
| 6,106,245 A | 8/2000 | Cabuz |
| 6,109,889 A | 8/2000 | Zengerie et al. |
| 6,116,756 A | 9/2000 | Peeters et al. |
| 6,124,663 A | 9/2000 | Haake et al. |
| 6,179,586 B1 | 1/2001 | Herb et al. |
| 6,184,607 B1 | 2/2001 | Cabuz et al. |
| 6,215,221 B1 | 4/2001 | Cabuz et al. |
| 6,237,619 B1 | 5/2001 | Maillefer et al. |
| 6,281,975 B1 | 8/2001 | Munk |

FOREIGN PATENT DOCUMENTS

| | | |
|---|---|---|
| EP | 0269076 | 6/1988 |
| EP | 1001326 | 5/1999 |
| EP | 1134548 | 9/2001 |
| WO | WO95/27199 | 3/1995 |
| WO | WO99/60397 | 4/1999 |
| WO | WO01/09598 | 7/2000 |
| WO | WO02/10714 | 2/2002 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Shapiro, "Practical Flow Cytometry", third edition, 1995, p. 237.

Cleopatra Cabuz et al., "Mesoscopic Sampler Based on 3D Array of Electrostatically Activated Diaphragms", The 10th Int. Conf. On Solid-State Sensors and Actuators, Transducers'99, Jun. 7-12, 1999, Sendai Japan, p. 1890-1.

T. Ohnstein et al., "Micromachined Silicon Microvalve", Proceedings of MEMS, 1990, IEEE Micro Electromechanical Systems, Napa Valley, California, Feb. 11-14, 1990, pp. 95-98.

Strzelecka, E. et al., "Parallel Free-Space Optical Interconnect Based on Arrays of Vertical-Cavity Lasers and Detectors with Monolithic Microlenses", Applied Optics, v. 37 (14), May 10, 1998, pp. 2811-2821. Copyright 1998 Optical Society of America.

Lehman, J. et al., "High-Frequency Modulation Characteristics of Red VCSELs", Electronics Letters, Feb. 13, 1997, vol. 33(4), pp. 298-300. Copyright 1997 IEE.

"Applying Microfluidic Chemical Analytical Systems To Imperfect Samples", P. Yager et al., Micro Total Analysis Systems 98, D. Harrison & A. van den Berg (ed.), Kluwer Academic Publishers, Dordrecht, 207-212, 1998.

"Design Of Microfluidic Sample Preconditioning Systems For Detection Of Biological Agents In Environmental Samples", Yager, M. et al., SPIE Proceedings, 3515, 252-259, 1998.

"Development Of A Flow Cytometry Based Miniature Chemical Fluid Analysis System Using Fluorescent Microbeads", M. Huang. et al., SPIE Biomedical Optics, BIOS 97, conference proceedings, 1997.

"Differential Blood Cell Counts Obtained Using A Microchannel Based Flow Cytometer", E. Altendorf et al., Solid State Sensors & Actuators, vol. 1, 531, 1997.

"Diffusion-Based Optical Chemical Detection In Silicon Flow Structures", B. Weigl et al., Analytical Methods & Instrumentation, $\mu$TTAS 96 special edition, 1996.

"Fluorescence Analyte Sensing In Whole Blood Based On Diffusion Separation In Silicon-Microfabricated Flow Structures", B. Welgl et al., SPIE Proceedings, J. Lakowitz (ed.), Fluorescence Sensing Technology III, 1997.

"Fluorescence And Absorbance Analyte Sensing In Whole Blood And Plasma Based On Diffusion Separation In Silicon-Microfabricated Flow Structures (T-Sensors™)", B. Weigl, et al., Biomedical Optics, vol. 6, No. 1, Jul. 1997.

"Implementation Of Novel Optical Detection Methods For Clinically Important Blood Analytes Using Microfabricated Flow Structures (T-Sensors™)", E. Altendorf & B. Weigl, MicroTAS 98, Banff, Canada, Apr. 1998.

"Integration Of Microelectrodes With Etched Microchannels For In-Stream Electrochemical Analysis", R.Darling et al., MicroTAS 98, Banff, Canada, Apr. 1998.

"Microfabrication Technology For Research And Diagnostics, Silicon Microchannel Optical Flow Cytometry", E. Altendorf et al., SPIE Proceedings, Biomedical Optics 96, Jan. 1996.

"Microfluidic Approaches To Immunoassays", A. Hatch et al., SPIE conference on Micromachining and Microfabrication Symposium at Santa Clara, CA, Sep. 20-22, 1999.

"Microfluidic Diffusion Based Electrochemical Detection Using Microfabricated Flow Structures (T-Sensors™)", B. Weigl, Analytical Chemistry, submitted 1999.

"Microfluidic Diffusion-Based Separation And Detection", B. Weigl & P. Yager, Science, vol. 283, pp 346-347, Jan 15, 1999.

"Optical And Electrochemical Diffusion-Based Detection Of Analytes In Complex Samples Using Microfabricated Flow Structures (T-SensorSTM)", B. Weigl, R. Darling, P. Yager, J. Kriebel & K. Mayes, Micro- and nanofabn'cated electro-optical mechanical systems for biomedical and environmental applications II- SPIE vol. 3606, Jan 25-26, 1999.

"Rapid Sequential Chemical Analysis Using Multiple Fluorescent Reporter Beads", B. Weigl et al., $\mu$TTAS 96 Conference Proceedings, 1996.

"Results Obtained Using A Prototype Microfluidics-Based Hematology Analyzer", E.Altendorf et al., SPIE Biomedical Optics 97, 1997.

"Silicon-Microfabricated Diffusion-Based Optical Chemical Sensor", B. Weigh & P. Yager, Reprint from "Sensors & Actuators" B 38-39, 452-457, 1997.

"Simultaneous Self-Referencing Analyte Determination In Complex Sample Solutions Using Microfabricated Flow Structures (T-Sensors™)", B. Weigl et al., Proceedings of MicroTAS 98, 81-4, Banff, Canada, 1998.

"Whole Blood Assays Using Microfluidics-Based T-SensorSTm Technology", B. Weigl, Medical Design Online, http://news.medicaldesignonline.com/featuresarticles/19990416-5922.html, Apr. 1999.

Terstappen, et al., "Four-Parameter White Blood Cell Differential Counting Based on Light Scattering Measurements", Alan R. Liss, Inc., Cytometery 9:39-43, 1988.

Toshiyoshi et al., "Surface micromachined 2D Lens Scanner Array", Proc. IEEE?LEOS International Coference on Optical EMMS/Sheraton Kauai Resort, Kauai, Hawaii, Aug. 21-24, 2000, 2 pages.

Toshiyoshi et al., "Micromechanical Lens Scanner for Fiber Optic Switches", Proc. $3^{rd}$ International Conference on Micro Opto Electro Mechanical Systems (MOEMS 99), Aug. 30-Sep. 1, 1999, Mainz, Germany, pp. 165-170.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array For Beam Steering and Precision Alignment in Optical Interconnect Systems", Solid-State Sensor and Actuator Workshop, Hilton Head Island, South Carolina, Jun. 4-8, 2000, pp. 101-104.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

* cited by examiner

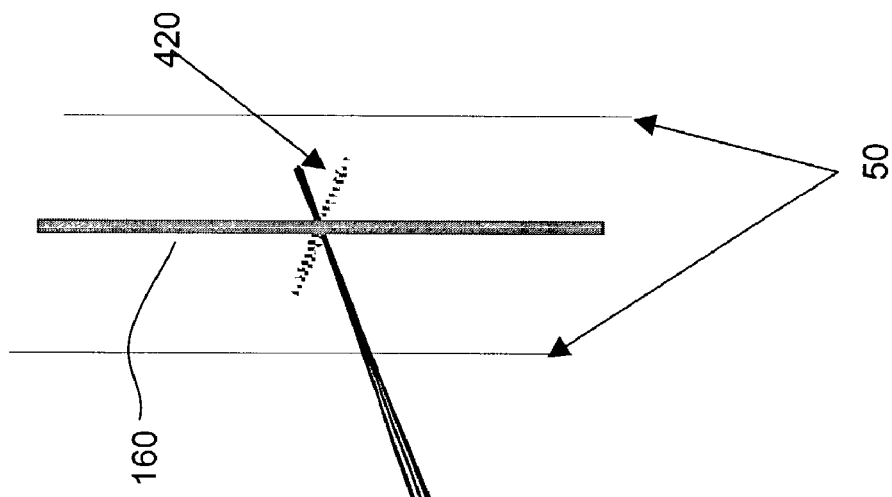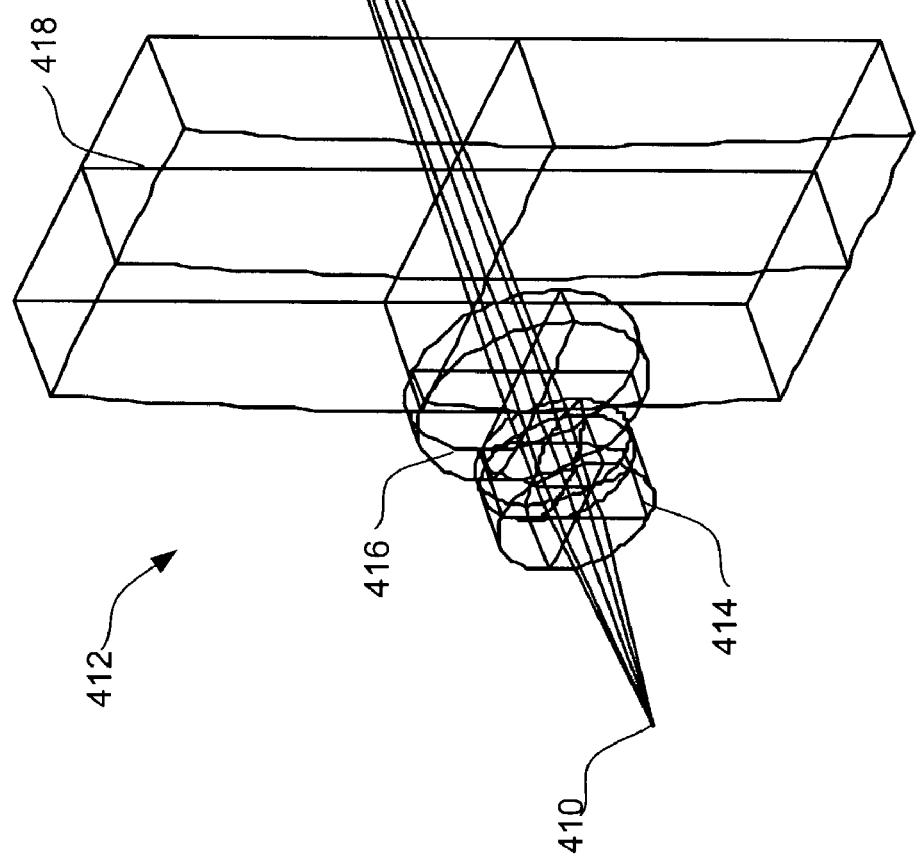
FIG. 15

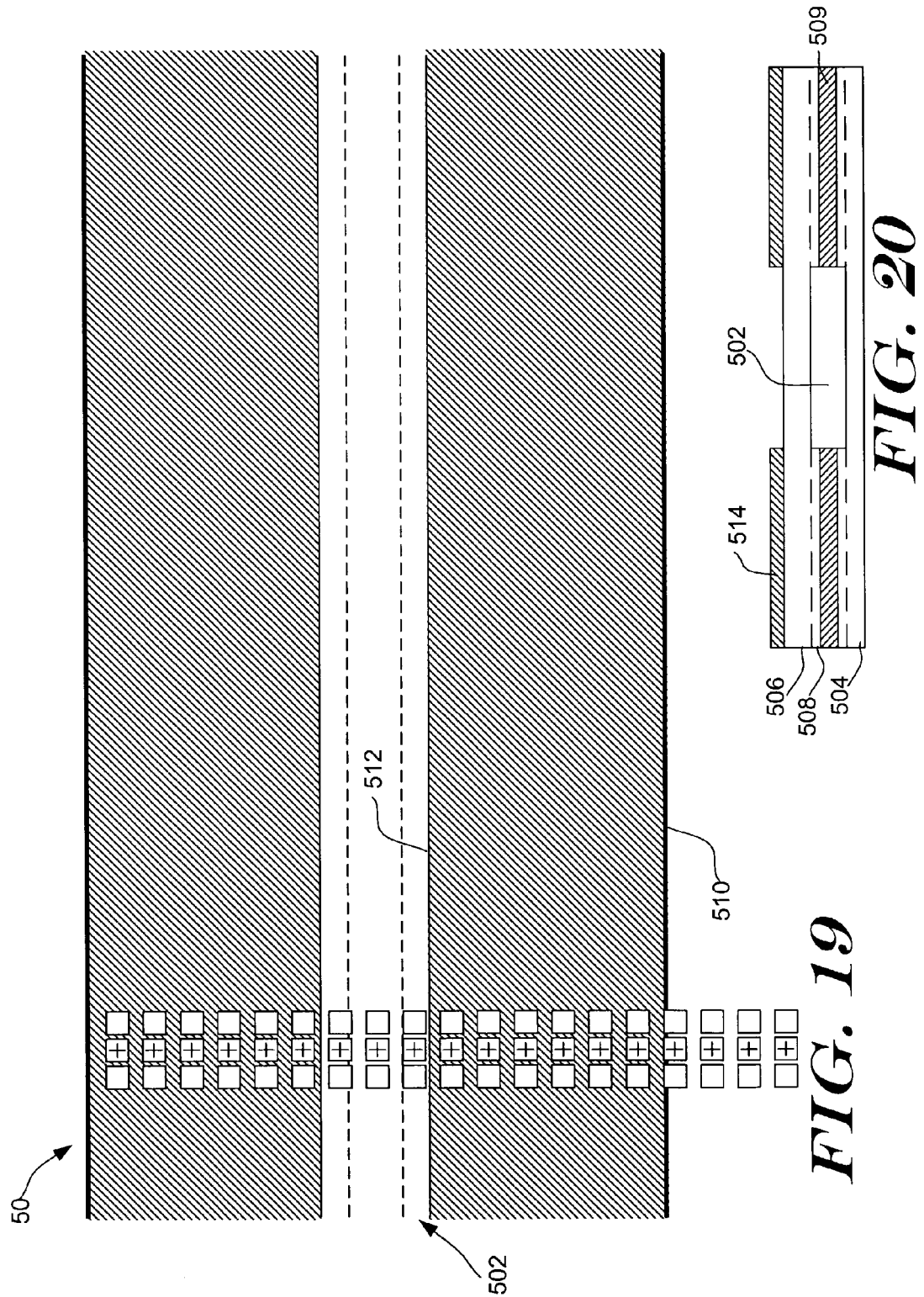

OPTICAL ALIGNMENT DETECTION SYSTEM

This Application is a continuation-in-part application of U.S. patent application Ser. No. 09/630,927, filed Aug. 2, 2000 now U.S. Pat. No. 6,549,275, and entitled "OPTICAL DETECTION SYSTEM FOR FLOW CYTOMETRY".

GOVERNMENT SUPPORT

This invention was made with government support under DARPA contract number MDA972-00-C-0029. The government may have certain rights in the invention.

BACKGROUND

The present invention relates generally to alignment systems, and more particularly, to optical alignment detection systems.

In many of today's systems, it is desirable to align a first object and a second object. In many cases, proper alignment is required for the proper and/or efficient operation of the system. For example, in printer applications, removable print cartridges must often be aligned with the printer assembly for the system to print properly. In another example, tape cartridges must often be aligned with a tape reader or the like to ensure that the tape can be read and/or to reduce wear on the tape. Most other forms of removable media have similar alignment concerns. Optical fiber alignment, component alignment, as well as many other applications and systems also require two or more objects to be properly aligned.

In many cases, the alignment of two objects is achieved via some sort of mechanical coupling. For example, in many cases, a first object includes a mechanical key such as a pin, tab or other mechanical feature, and the second object includes a corresponding hole, slot, recess or other corresponding feature. When the first object is brought into engagement with the second object, the mechanical alignment features force the first object to align with the second object.

A limitation of this approach is that the accuracy of the alignment is limited by the mechanical tolerances of the mechanical coupling features. Thus, to provide a highly accurate alignment, the tolerances of the mechanical coupling features must also be tightly controlled. This, however, can significantly increase the cost and complexity of producing the first and second objects. Another limitation is that if the first object is misaligned relative to the second object for one reason or another, there is often no way of knowing of the misalignment and/or for correcting for the misalignment.

SUMMARY

The present invention provides an optical alignment detection system for detecting the alignment of a first object relative to a second object. The present invention preferably uses one or more light sources and one or more light detectors, either or both of which is secured relative to the second object, to detect the position of one or more light scattering elements on the first object. In one illustrative embodiment, an array of light sources and one more light detectors are used. By identifying the location of the light source(s) that produce a predetermined light scattering profile through the one or more light scattering elements on the second object, the location of the first object relative to the second object can be determined. Because the light sources and/or light detectors may be spaced relatively close together, the alignment between the first object and second object may be relatively accurately determined. Once the relative location of the second object is determined, and in some embodiments, other light sources in the array of lights sources that correspond to an examination or measurement region may be identified and used to make a measurement or the like. In other embodiments, an array of light detectors may be used to determine the relative location of the second object. In yet other embodiments, an actuator may be used to move the second object relative to the second object to bring the first object and second object into proper alignment.

In some embodiments, each of the light sources is adapted to provide a light beam. The light sources may be positioned so that as long as the first and second objects are aligned within a predetermined range, one or more of the light beams will intersect at least one of the light scattering elements, which then produces a scattered light profile. One or more detectors are preferably positioned such that at least one of the detectors will detect the scattered light profile. A controller may be used to identify which of the light sources actually produced the scattered light profile, and to correlate the location of the identified light source(s) to an alignment position of the first object relative to a second object.

During operation, and in one illustrative embodiment, each of the light sources or a sub-set of light sources are sequentially activated. Depending on the alignment of the first object relative to the second object, a particular light source or light sources will produce a light beam that intersects a light scattering element. The light source or light sources that produce the light beam that intersects the light scattering element can be identified by monitoring the output of the corresponding detectors. By only activating one or a sub-set of light sources at any given time, the light source or light sources that produced the light beam that intersects the light scattering element may be more easily identified. By knowing which light source or light sources produced the light beam that intersects the light scattering element, and the location thereof, the alignment of the first object relative to the second object can be determined.

Once the relative alignment is determined, and in some embodiments, the present invention may calculate an offset, for example, to identify one or more light sources that have a location that is adjacent another region such as an examination or measurement region of the first object. Once identified, the light source(s) may be used to, for example, detect one or more parameters and/or characteristics of the first object and/or second object. The one or more parameters or characteristics may include, for example, one or more optical characteristics, one or more electric or magnetic characteristics, one or more physical characteristics, or any other desired characteristic. In this way, the present invention may be used to detect the alignment between the first and second objects, and then compensate for any misalignment by selecting appropriate light sources and/or detectors.

In some embodiments, one or more of the light sources that do not produce a light beam that intersects the light scattering element(s) are used to determine other parameters, such as one or more characteristics of the first object. In one illustrative embodiment, the light sources are configured in a linear or other type of array that spans a region that includes the one or more light scattering elements when the misalignment between the first object and second object is within a predetermined range. The linear or other type of array may also span an examination or measurement region of the first object. During operation, selected light sources of the linear or other type of array may be used to determine the alignment of the first object relative to the second object by identifying the location of the one or more light scattering elements. Then, by calculating an offset, for example, the identity of selected other light sources of the linear or other type of array that have a location that is adjacent the examination or measurement region of the first object can be identified. The identified light sources can then be used to determine selected characteristics or properties of the first object in the examination region. In one illustrative embodiment, the examination region may include a flow channel.

In some embodiments, the light beam from all or selected light sources may pass through a beam former or the like. When the light sources are in a linear array that extends along an array axis, the beam former may, for example, increase the beam spot size of each light source in the direction of the axis, and in some cases decrease the beam spot size in a direction perpendicular to the axis, but this is not required. In some embodiments, the beam former may increases the beam spot size in the direction of the axis such that the light output of each light source at least partially overlaps the light output of an adjacent light source. This may help produce a relatively constant light illumination across an elongated area, such as the region that is expected to include the one or more light scattering elements and/or the examination region. In some embodiments, the beam former may include one or more cylinder lenses, if desired.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 15 is a schematic diagram showing an illustrative beam former for use with a single light source;

FIG. 19 is a schematic diagram of a laminated cartridge having a flow channel 502 and one or more light blocking layers or regions;

FIG. 20 is a cross-sectional side view of the cartridge of FIG. 19;

DETAILED DESCRIPTION

Figure 1:
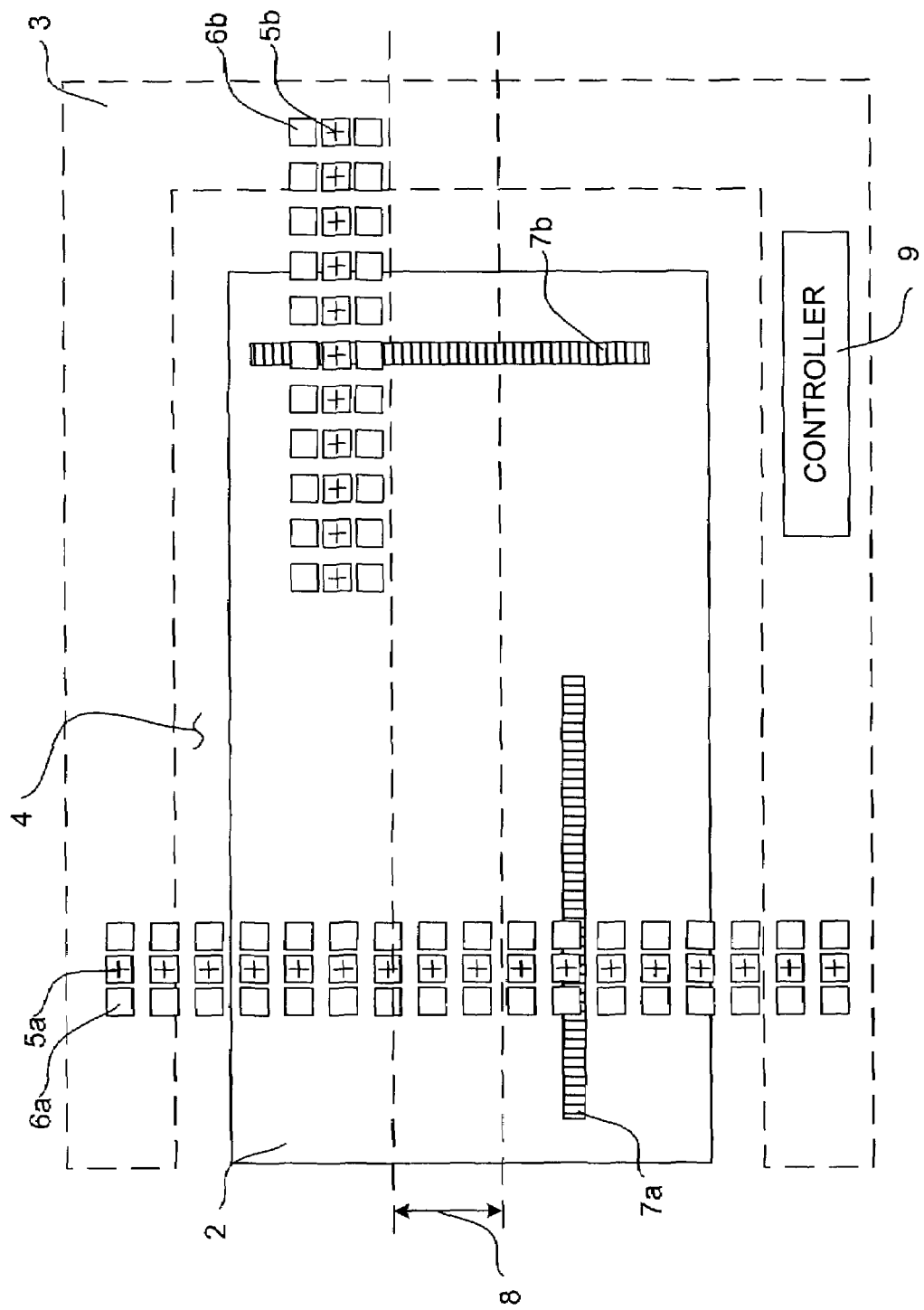
FIG. 1 is a schematic diagraph showing an illustrative embodiment of the present invention.

FIG. 1 is a schematic diagraph showing an illustrative embodiment of the present invention. The illustrative embodiment includes a first object 2 and a second object 3, wherein the second object 3 includes a slot 4 for receiving the first object 2. While a slot 4 is used in this example, it is not required and some embodiments may not include a slot. The second object 3 shown in FIG. 1 includes a linear array of light sources 5a and a linear array of light detectors 6a. While a linear array is used in this example, any suitable array or configuration may be used. Each light source is represented by a plus sign (+) and each detector is represented by a box. The light sources 5a may include, for example, Vertical Cavity Surface Emitting Lasers (VC-SELs), Light Emitting Diodes (LEDs), or any other suitable light source. The light detectors 6a may include, for example, photo diodes or any other suitable light detector. The detectors 6a may be square, circular, annular or any other suitable shape, as desired. In addition, the detectors 6a may be a single or small number of detectors that detect light from a wide range of locations. In some cases, optics may be used to direct the light from the wide range of locations to the single or small number of detectors, as further described below with respect to FIG. 16.

In the embodiment shown, the linear array of light sources 5a are mounted on one side (e.g. upper side) of the slot 4 in the second object 3, and the linear array of light detectors 6a are mounted on an opposite side (e.g., lower side) of the slot 4 of the second object 3. However, in some embodiments, the light sources 5a and the light detectors 6a may be mounted on the same side of the slot 4, such as when the light scattering elements are reflective. The pitch and/or spacing of the linear array of light sources 5a and light detectors 6a may be set to achieve the desired accuracy of alignment detection, as desired.

In FIG. 1, the first object 2 includes an elongated light scattering element 7a that extends substantially perpendicular to the linear array of light sources 5a and light detectors 6a when the first object 2 is inserted into the slot 4 of the second object 3. The term "light scattering element", as used herein, may include any optical element that diverts, changes, reflects, refracts, absorbs, or otherwise alters a light beam. The one or more light scattering elements 7a may include, for example, one more lenses, edges or steps, diffraction gratings, absorptive filters, reflectors, flow channels, or any other type of light scattering element. Other portions of the first object 2 may be clear, opaque or substantially non-transparent, as desired.

In the illustrative embodiment shown in FIG. 1, each of the light sources 5a is adapted to provide a light beam that is directed toward the slot 4 and to one or more corresponding detectors 6a. The linear array of light sources 5a may be positioned with respect to the slot 4 so that as long as the first object 2 and second object 3 are aligned within a predetermined range 8, one or more of the light beams will intersect at least one of the light scattering elements 7a, which then produces a scattered light profile at one or more of the corresponding detectors 6a. The detectors 6a may be positioned such that at least one of the detectors 6a will detect the scattered light profile. A controller 9 may be used to identify which of the light sources actually produced the detected scattered light profile, and may correlate the location of the identified light source(s) to an alignment position of the first object 2 relative to a second object 3.

During operation, and in one illustrative embodiment, each of the light sources 5a or a sub-set of light sources may be sequentially activated by the controller 9. Depending on the alignment of the first object 2 relative to the second object 3, a particular light source 5a or light sources may produce a light beam that intersects the light scattering element 7a. The light source 5a or light sources that produce the light beam that intersects the light scattering element 7a can be identified by monitoring the output of the corresponding detectors 6a. By only activating one or a sub-set of light sources 5a at any given time, the light source 5a or light sources that produced the light beam that intersects the light scattering element 7a may be more easily identified. However, it is contemplated that all of the light sources may be simultaneously activated and still be within the scope of the present invention. In any event, by knowing which light source 5a or light sources produced the light beam that intersects the light scattering element 7a, and the location thereof, the alignment of the first object 2 relative to the second object 3 can be determined.

If the light scattering element 7a is uniform along its length in the X-direction (e.g. the left-right direction), the linear array of light sources 5a and the detectors 6a may be used to determine the alignment position of the first object 2 relative to the second object 3 in the Y direction (e.g. the up-down direction in FIG. 1). If, however, the light scattering element 7a is not uniform along its length, and adapted to produce a different light scatter profile depending on where the light strikes the light scattering element 7a along its length, the linear array of light sources 5a and the detectors 6a may be used to determine the alignment position of the first object 2 relative to the second object 3 in both the X and Y direction. In this embodiment, the controller 9 may not only identify which of the light sources actually produced the detected scattered light profile to determine the Y position, as described above, but also may correlate the particular light scatter profile that is detected to an X position.

Alternatively, or in addition, a second elongated light scattering element 7b may be secured relative to the first object 2. The second elongated light scattering element 7b may extend in the Y direction, with a second linear array of light sources 5b and light detectors 6b extending substantially perpendicular to the second elongated light scattering element 7b. Then, the second linear array of light sources 5b and light detectors 6b may be used in conjunction with the second elongated light scattering element 7b to determine the X position of the first object 2 relative to the second object 3. In some embodiments, the second elongated light scattering element 7b may be non-uniform along its length to help also identify the Y position of the first object 2 relative to the second object 3, if desired. If either or both of the first light scattering element 7a and the second light scattering element 7b are non-uniform along their length, some level or redundancy may be provided in the optical alignment detection system.

It is contemplated that the first object 2 and the second object 3 may be any type of objects. In one example, the first object 2 may be a removable media component such as a removable print cartridge, a removable data storage cartridge such as a removable tape cartridge or removable flash memory cartridge, a removable bio-analysis cartridge or slide or any other form of removable object. The second object may then accept the removable media. Beyond removable media applications, optical fiber alignment applications, component alignment applications, as well as many other applications are also within the scope of the present invention.

Figure 2:
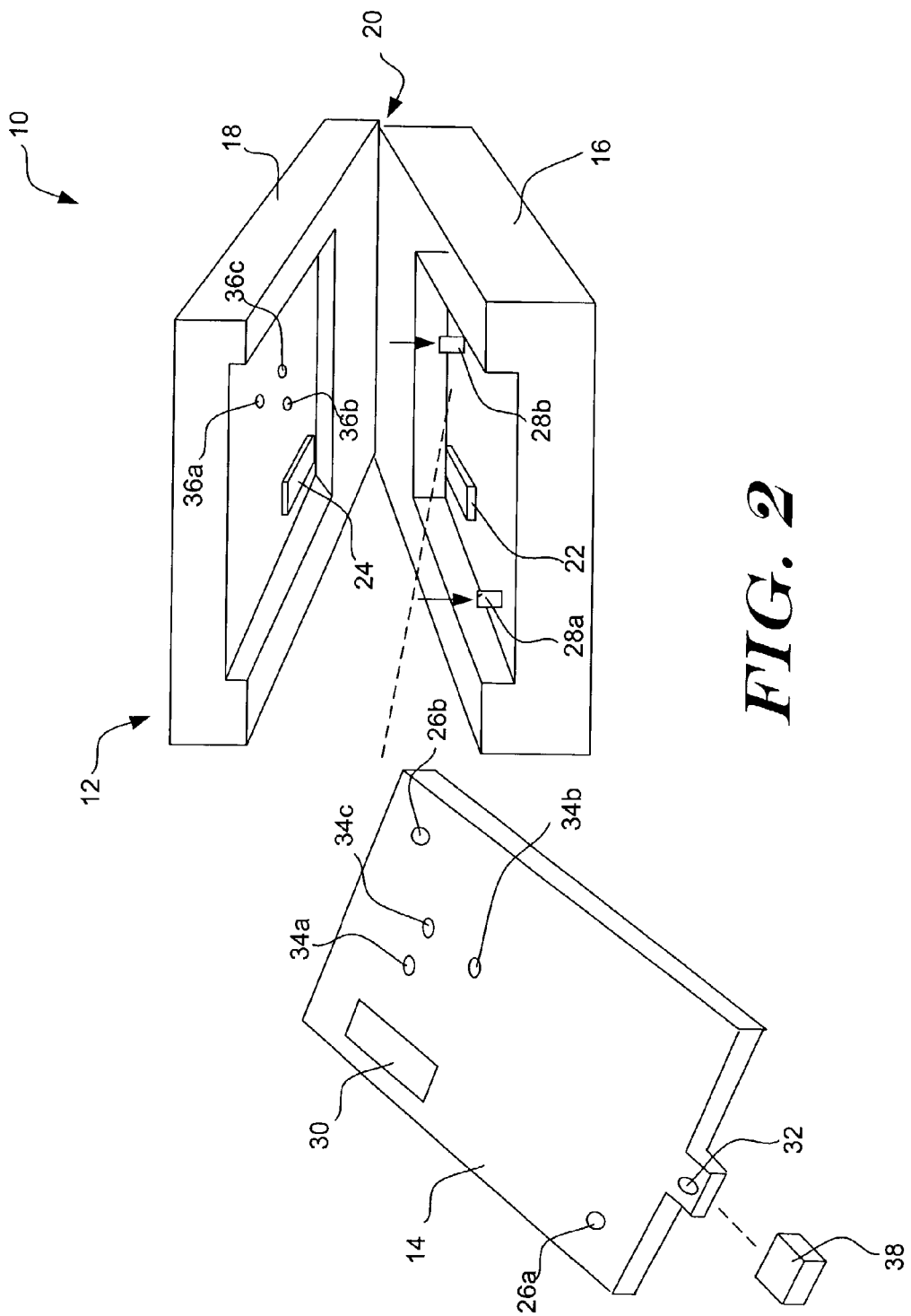
FIG. 2 is a perspective view of an illustrative portable cytometer in accordance with the present invention.

FIG. 2 shows an illustrative embodiment of the present invention that includes a removable bio-analysis cartridge. FIG. 2 is a perspective view of an illustrative portable cytometer 10, which includes a housing 12 and a removable or replaceable cartridge 14. The illustrative housing 12 includes a base 16, a cover 18, and a hinge 20 that attaches the base 16 to the cover 18. The base 16 includes an array of light sources 22, associated optics and the necessary electronics for operation of the cytometer. The cover 12 includes a manual pressurizing element, pressure-chambers with control microvalves, and an array of light detectors 24 with associated optics.

The removable cartridge 14 preferably receives a sample fluid via a sample collector port 32. A cap 38 may be used to protect the sample collector port 32 when the removable cartridge 14 is not in use. The removable cartridge 14 preferably performs blood dilution, red cell lysing, and hydrodynamic focusing for core formation. The removable cartridge 14 may be constructed similar to the fluidic circuits available from Micronics Technologies, some of which are fabricated using a laminated structure with etched channels.

The removable cartridge 14 is inserted into the housing when the cover 18 is in the open position. The removable cartridge 14 may include holes 26a and 26b for receiving registration pins 28a and 28b in the base 16, which may help provide alignment and coupling between the different parts of the instrument. In some embodiments, the holes 26a and 26b and registration pins 28a and 28b are not required or even desired, and the alignment detection system described herein is used to detect the alignment of the removable cartridge 14 with respect to the base 16 and cover 18. The removable cartridge 14 may also include a transparent flow stream window 30, which is in alignment with the array of the light sources 22 and light detectors 24, and one or more light scattering elements (not shown). When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22, light detectors 24 and associated control and processing electronics perform solid state alignment detection and correction for the particular position of cartridge 14, as well as differentiation and counting of white blood cells based on light scattering signals. Rather than using a hinged construction for the housing 12, it is contemplated that a sliding cartridge slot or any other suitable construction may be used.

Figure 3:
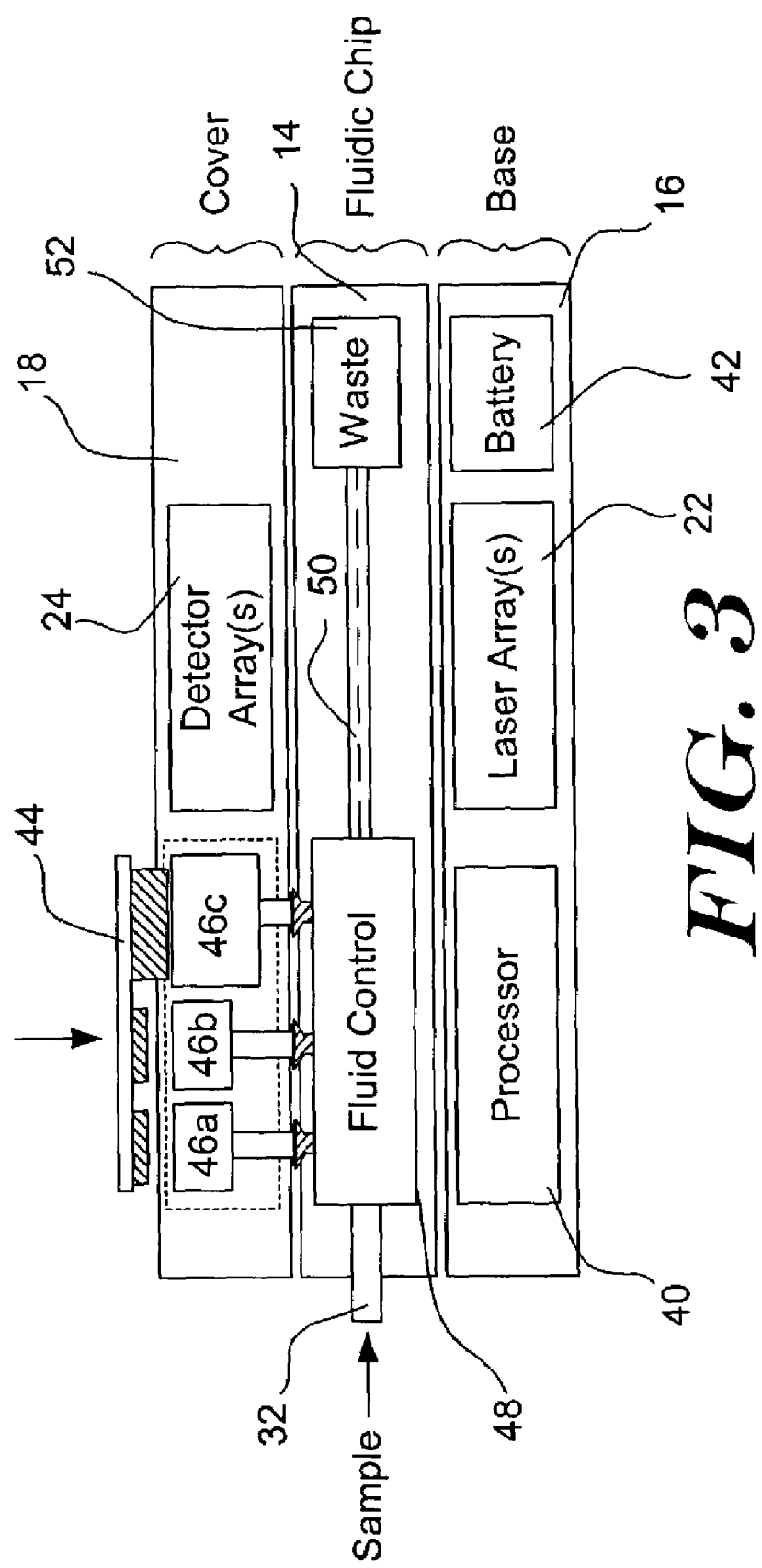
FIG. 3 is a schematic view of the illustrative portable cytometer of FIG. 2.

FIG. 3 is a schematic view of the illustrative portable cytometer of FIG. 2. As above, the base 16 may include an array of light sources 22, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and light detectors 24 with associated optics.

The removable cartridge 14 may receive a sample fluid via the sample collector port 32. When pressurized by the cover 18, the removable cartridge 14 performs blood dilution, red cell lysing, and hydrodynamic focusing for core formation in a preferred embodiment. Once formed, the core is provided down a flow stream path 50, which passes the flow stream window 30 of FIG. 2. The array of light sources 22 and associated optics in the base provide light through the core stream via the flow stream window 30. The detector(s) and associated optics receive scattered and non-scattered light from the core, also via the flow stream window 30. The controller or processor 40 receives output signals from detector(s), and differentiates and counts selected white blood cells that are present in the core stream.

It is contemplated that the removable cartridge 14 may include a fluid control block 48 for helping control the velocity of each of the fluids. In the illustrative embodiment, the fluid control block 48 includes flow sensors for sensing the velocity of the various fluids and reports the velocities to the controller or processor 40. The controller or processor 40 may then adjust the microvalves associated with pressure-chambers 46a, 46b and 46c to achieve the desired pressures and thus desired fluid velocities for proper operation of the cytometer.

Because blood and other biological waste can spread disease, the removable cartridge 14 preferably has a waste reservoir 52 downstream of the flow stream window 30. The waste reservoir 52 receives and stores the fluid of the flow stream in the removable cartridge 14. When a test is completed, the removable cartridge may be removed and disposed of, preferably in a container compatible with biological waste.

Figure 4:
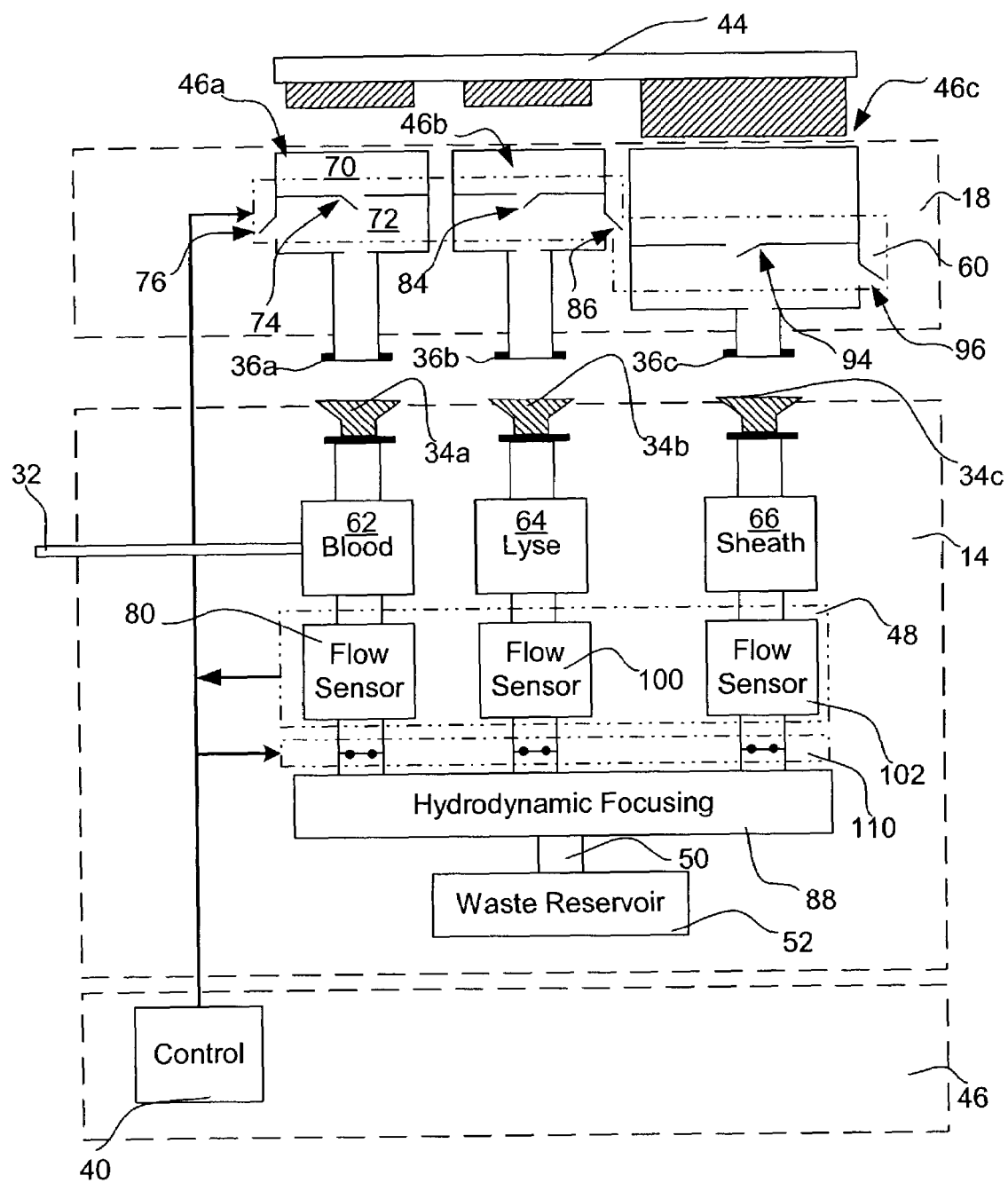
FIG. 4 is a more detailed schematic diagram showing the portable cytometer of FIG. 3 with the cover not yet depressed.
Figure 5:
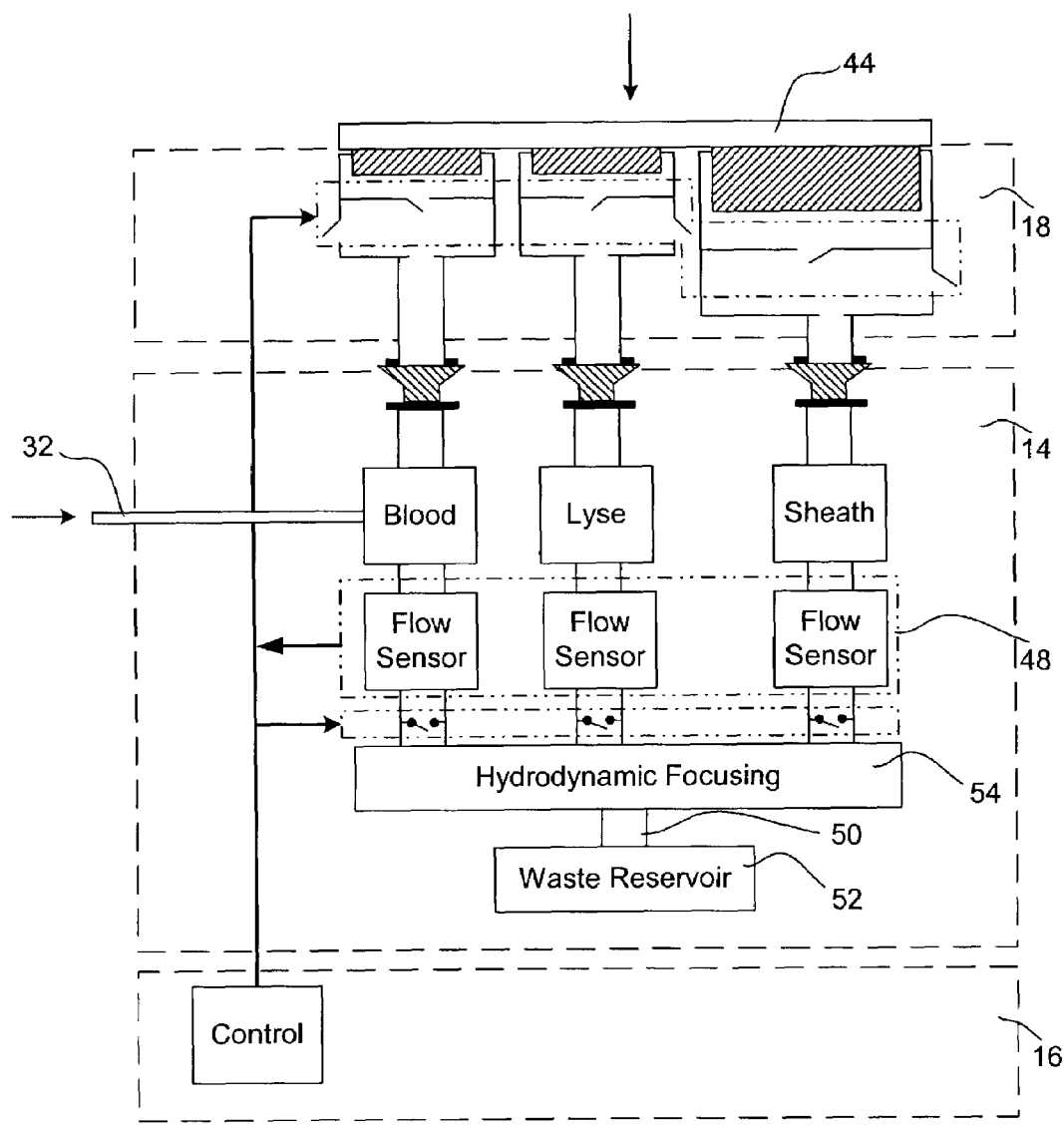
FIG. 5 is a more detailed schematic diagram showing the portable cytometer of FIG. 3 with the cover depressed.

FIG. 4 is a more detailed schematic diagram showing the portable cytometer of FIG. 3 with the cover 18 not yet depressed. FIG. 5 is a more detailed schematic diagram showing the portable cytometer of FIG. 3 with the cover depressed. The cover 18 is shown having a manual pressurizing element 44, pressure-chambers 46a, 46b and 46c, and control microvalves generally shown at 60. The array of light sources and detectors are not shown in these Figures.

There are three pressure chambers 46a, 46b and 46c, one for each fluid to be pressurized. In the illustrative embodiment, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve is preferably an array of electrostatically actuated microvalves that are individually addressable and controllable. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 are preferably filled before the removable cartridge 14 is shipped for use, while the blood reservoir 62 is filled from sample collector port 32. A blood sample may be provided to the sample collector port 32, and through capillary action, the blood sample is sucked into the blood reservoir 62. Once the blood sample is in the blood reservoir 62, the cover 18 may be closed and the system may be pressurized.

A flow sensor is provided in-line with each fluid prior to hydrodynamic focussing. Each flow sensor 80, 100 and 102 measures the velocity of the corresponding fluid. The flow sensors are preferably thermal anemometer type flow sensors, and more preferably microbridge type flow sensor. An output signal from each flow sensor 80, 100 and 102 is provided to controller or processor 40.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If two much pressure builds up in the secondary pressure chambers, the corresponding vent valve 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another embodiment, downstream valves 110 are opened by mechanical action when the cover is closed.

Figure 6:
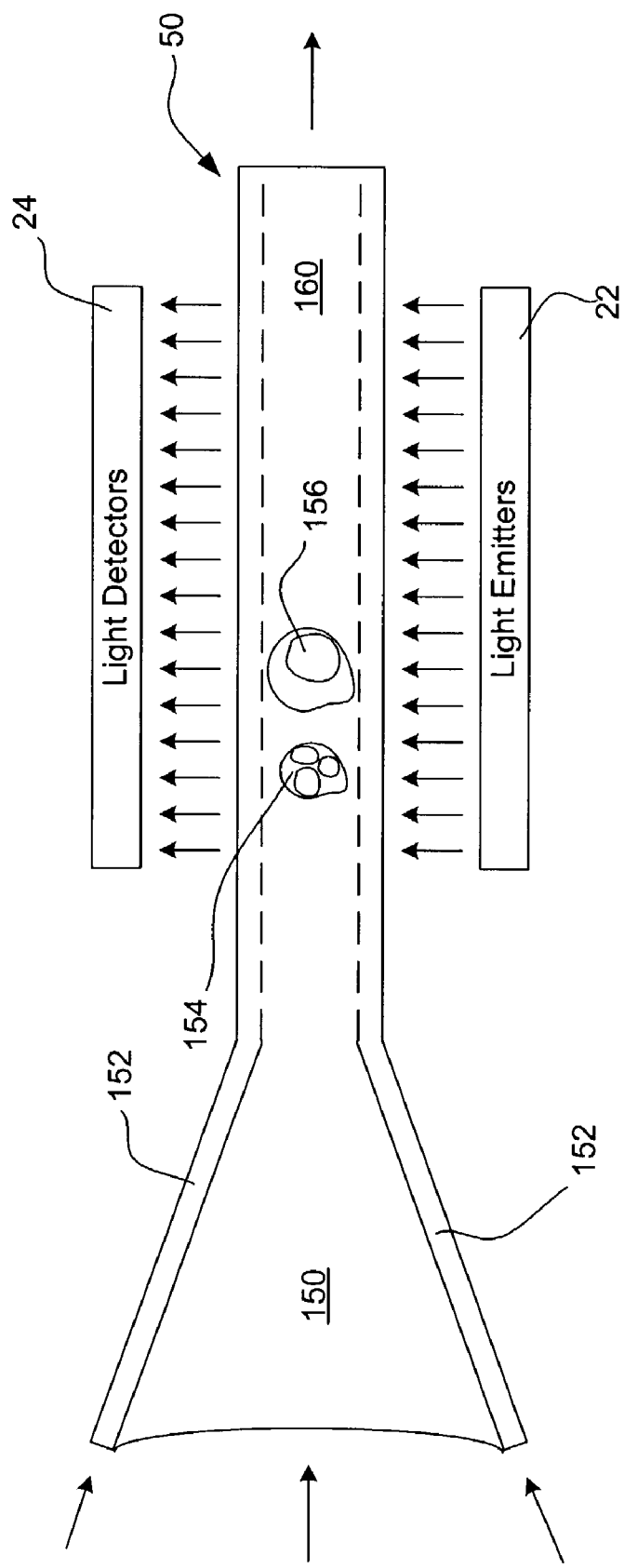
FIG. 6 is a schematic diagram showing the formation of a flow stream by the hydrodynamic focusing block 88 of FIG. 4.

FIG. 6 is a schematic diagram showing the formation of a flow stream and core by the hydrodynamic focusing block 88 of FIG. 4. The hydrodynamic focusing block 88 receives blood, lyse and sheath at controlled velocities from the fluid driver. The blood is mixed with lyse, causing the red blood cells to be removed. This is often referred to as red cell lysing. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the white blood cells 154 and 156 are in single file. The velocity of the sheath fluid is preferably about 9 times that of the core stream 160. However, the velocity of the sheath fluid and core stream 160 preferably remains sufficiently low to maintain laminar flow in the flow channel.

Light emitters 22 and associated optics are preferably provided adjacent one side of the flow stream 50. One or more light detector(s) 24 and associated optics are provided on another side of the flow stream 50 for receiving the light from the light emitters 22 via the flow stream 50. The output signals from the light detector(s) 24 are provided to controller or processor 40, wherein they are analyzed to identify and/or count selected white blood cells in the core stream 160.

Figure 7:
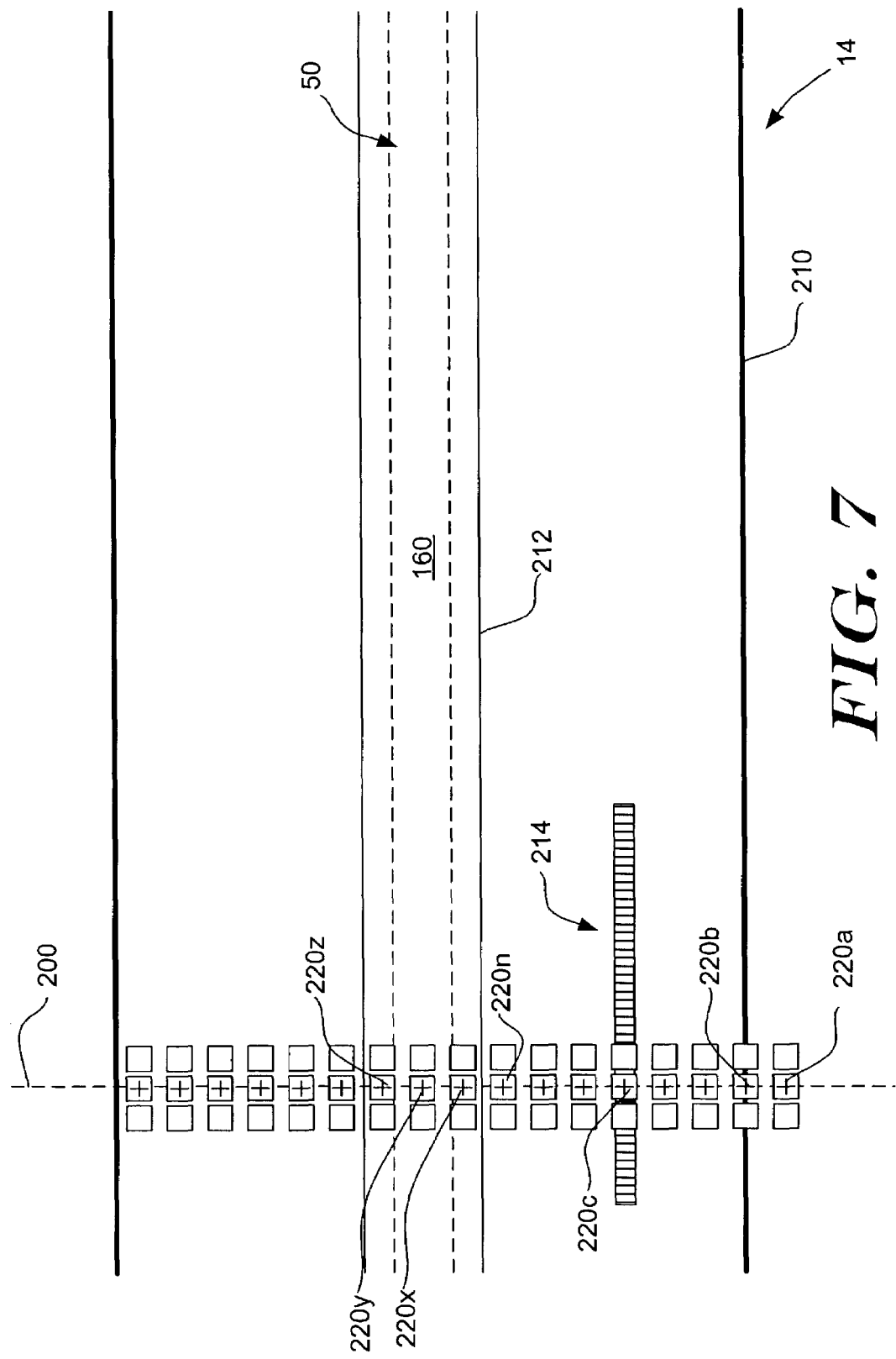
FIG. 7 is a schematic diagram showing an illustrative embodiment of the present invention.

FIG. 7 is a schematic diagram showing an array of light sources and an array of light detectors for analysis of the core stream 160 of FIG. 6, and for identifying the relative alignment position of the cartridge 14 relative to the base 16 and/or cover 18 (see, for example, FIG. 2). The light sources are shown as plus (+) signs and the detectors are shown as boxes. In the embodiment shown, the array of light sources is provided adjacent one side of the flow stream 50, such as in or on the base 16, and the array of light detectors is provided adjacent the opposite side of the flow stream, such as in or on the cover 18. Each of the light detectors preferably corresponds to one of the light sources. In some embodiments, only a single or small number of light detectors are provided that are capable of detecting light from a relatively large area, such as the area corresponding to the array of light sources. In the embodiment shown, the array of light sources and the array of light detectors are arranged along a light source axis 200 that is substantially orthogonal to the axis of the flow stream 50. It is contemplated, however, that the array of light sources and the array of light detectors may be arranged along a light source axis that is offset at any angle relative to the axis of the flow stream 50. Although the array of light sources and the array of light detectors are shown as linear arrays, any suitable arrangement may be used.

The array of light sources is preferably an array of lasers such as Vertical Cavity Surface Emitting Lasers (VCSEL) fabricated on a common substrate. Because of their vertical emission, VCSELs are ideally suited for packaging in compact instruments such as a portable cytometer. Preferably, the VCSELs are "red" VCSELs that operate at wavelengths that are less than the conventional 850 nm, and more preferably in the 670 nm to 780 nm range, but this is not required. Red VCSELs may have a wavelength, power and polarization characteristic that is ideally suited for scatter measurements. It is contemplated, however, that Light Emitting Diodes (LEDs) or any other suitable light source may be used. The light detectors may be, for example, photo diodes or any other suitable light detector. The detectors may be square, circular, annular or any other suitable shape, as desired.

In some embodiments, each of the light sources is adapted to provide a light beam. To identify the relative alignment position of, for example, the cartridge 14 relative to the base 16 and/or cover 18 (e.g., see FIG. 2), the array of light sources may extend a sufficient range so that one or more of the light beams will intersect at least one of the light scattering element of the cartridge 14. In the illustrative embodiment, the cartridge 14 includes a number of light scattering elements including, for example, cartridge edge 210, flow channel edge 212, and embossed light scattering elements 214. Each of the light scattering elements may produce a scattered light profile.

The detectors may be located such that at least one of the detectors will detect the scattered light profile of at least one of the light scattering elements. A controller may be used to identify which of the light sources actually produced the detected scattered light profile, and to correlate the location of the identified light source(s) to an alignment position of the cartridge 14 relative to the base 16 and/or cover 18.

During operation, and in one illustrative embodiment, each of the light sources or a sub-set of light sources may be sequentially activated. Depending on the alignment of the cartridge 14 to the base 16 and/or cover 18, a particular light source or light sources may produce a light beam that intersects a light scattering element, such as light scattering element 214. The light source or light sources that produce the light beam that intersects the light scattering element 214 can be identified by monitoring the output of the corresponding detectors. By only activating one or a sub-set of light sources at any given time, the light source or light sources that produced the light beam that intersects the light scattering element 214 may be more easily identified. By knowing which light source or light sources produced the light beam that intersects the light scattering element 214, and the location thereof, the alignment of the cartridge 14 relative to the base 16 and/or cover 18 can be determined.

Figure 8:
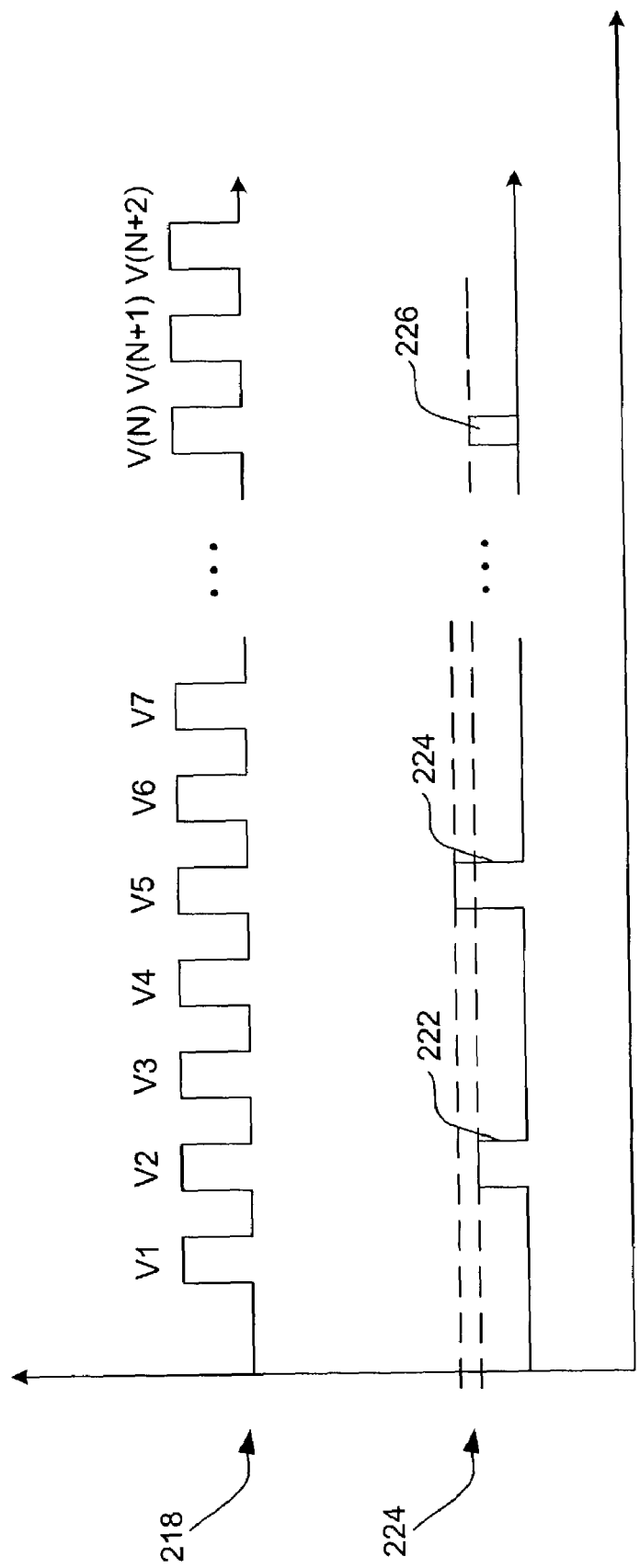
FIG. 8 is a timing diagram showing an illustrative method for activating the light sources of FIG. 7.

FIG. 8 is a timing diagram showing an illustrative method for activating the light sources of FIG. 7. In the illustrative embodiment, each of the light sources is sequentially activated, beginning with the light source 220 which is located at the bottom of the array of light sources shown in FIG. 7. The sequential activation of the light sources is shown generally at 218, where the notation V1, V2, etc., corresponds to the activation of VCSEL1 220$a$, VCSEL2 220$b$, etc., of FIG. 7. The response of the corresponding detectors is shown generally at 224.

When light source 220*a* is activated, no scattered light profile is detected at the corresponding detectors because, as shown in FIG. 7, the cartridge 14 is not situated between light source 220*a* and the corresponding detectors. While FIG. 7 shows three light detectors for each light source, only the left and right detectors may be used for detecting a scattered light profile in some embodiments. Light source 220*b* may then be activated. When this occurs, the corresponding detectors detect a scatter light profile 222. The characteristics of the scatter light profile 222 may identify the light scattering element as the cartridge edge 210.

When the third and forth light sources are activated, no scattered light profile is detected at the corresponding detectors. When the fifth light source 220*c* is activated, the corresponding detectors detect a scatter light profile 224. The characteristics of the scatter light profile 224 may identify the light scattering element as an embossed light scattering element 214. Continuing with the example, when light source 220N is activated, the corresponding detectors detect a scatter light profile 226. The characteristics of the scatter light profile 226 may identify the light scattering element as a fluid channel edge 212. For illustration purposes, the light scatter profiles 222, 224 and 226 are shown as having differing amplitudes. However, it is contemplated that any suitable parameter or characteristic may be used to differentiate between the light scatter profiles, as desired. Alternatively, only the locations of the light scattering elements are identified, and no differentiation between light scattering elements is provided. In some embodiments, only the light scatter profile 224 of the embossed light scattering element 214 may be identified, and the detection of the other light scattering elements may be disregarded.

Once this relative alignment of the cartridge 14 is determined, the present invention may identify which of the one or more light source and/or light detector elements have a location that is adjacent the flow stream 50. For example, in the illustrative embodiment of FIG. 7, the present invention may identify light sources 220*x*, 220*y* and 220*z* as having a location that is adjacent the flow stream 50. Depending on the relative alignment of the cartridge 14 and the base 16 and/or cover 18, different light sources and/or light detectors may be selected. For example, if the cartridge 14 were moved up so that light source 220*b* were positioned above the embossed light scattering element 214, then the three light sources immediately above light source 220*c* would have a location adjacent the flow stream 50, and would be selected. Once the light sources have been identified and selected, the selected light sources and/or light detectors may be used to, for example, detect one or more parameters and/or characteristics of the flow stream.

Figure 9:
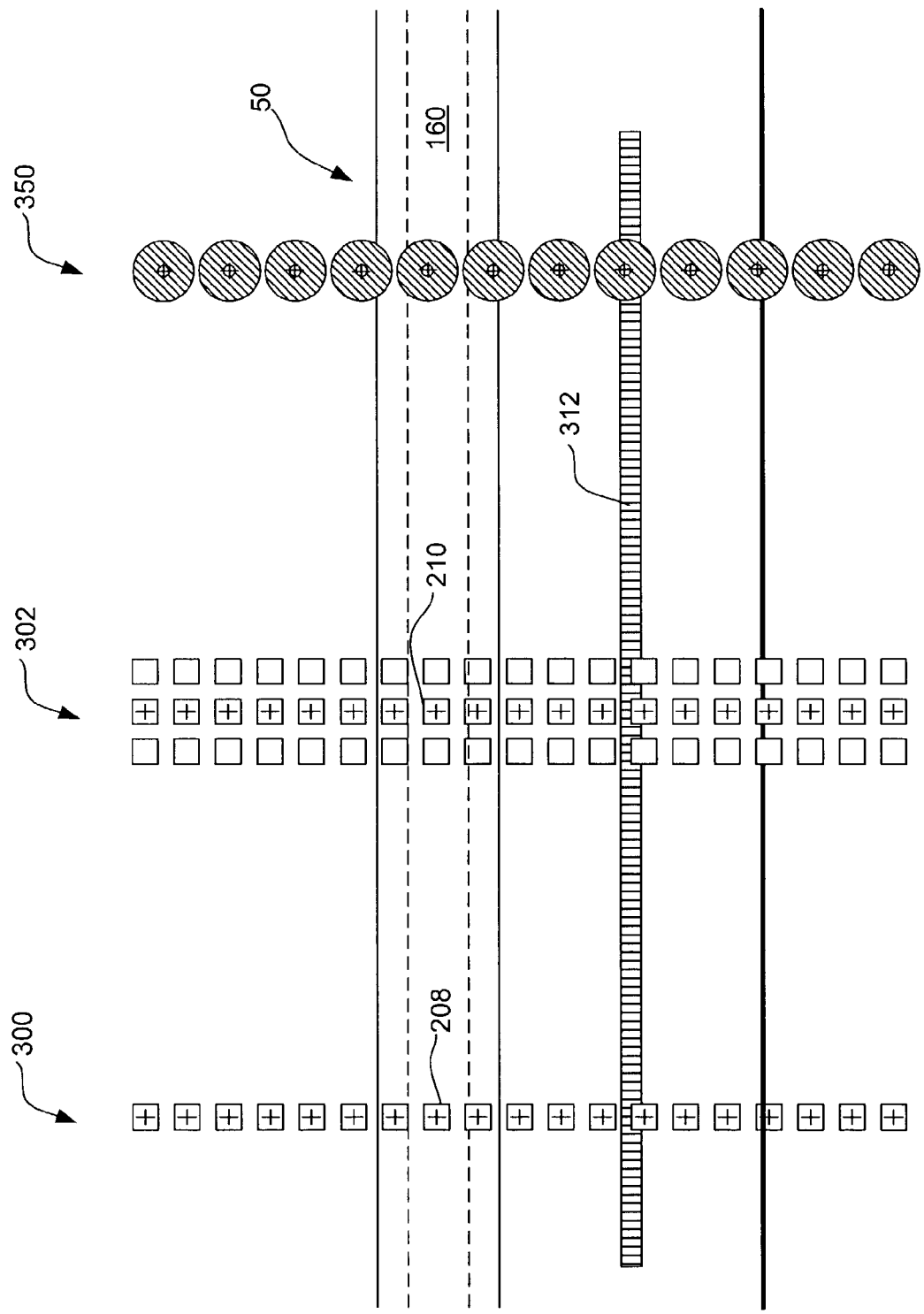
FIG. 9 is a schematic diagram showing three separate arrays of light sources and detectors, each positioned along a different light source axis relative to the central flow axis of the flow stream of FIG. 6.

FIG. 9 shows another illustrative embodiment of the present invention. This embodiment includes three separate arrays of light sources and light detectors. While three arrays are shown, it is recognized that any suitable number may be used, depending on the application. In the illustrative embodiment, each array of light sources and light detectors is positioned along a different light source axis relative to the central flow axis of the flow stream.

A first array of light sources and light detectors is shown at 300. In the illustrative embodiment shown, the light sources and light detectors of the first array 300 are arranged in a linear array along a first light source axis. The array of light detectors is positioned in line with the linear array of light sources. The light sources and light detectors of the first array 300 may be used to measure, for example, the lateral alignment of the cells in the flow stream 50, the particle size, and in some cases, the velocity of the particles. Alternatively, or in addition, the first array of light sources and light detectors 300 may be used to detect the position of a light scattering element, such as light scattering element 312, to help determine the alignment of the cartridge 14 relative to the base 16 and/or cover 18. For example, the light scattering element 312 may produce a light scattering profile that can be detected by one or more corresponding detectors. Once the location of the light scattering element 312 is identified, the alignment of the cartridge 14 relative to the base 16 and/or cover 18 can be determined.

A second array of light sources and light detectors is shown at 302. The second array of light sources may be arranged in a linear array along a second light source axis relative to the flow axis of the flow stream 50. In the illustrative embodiment, the light detectors of the second array 302 include three linear arrays of light detectors. One linear array of light detectors is positioned in line with the linear array of light sources. The other two linear arrays of light detectors are placed on either side of the in-line array of light detectors. The second array of light sources and light detectors 302 is similar that shown and described with respect to FIG. 7. As detailed with respect to FIG. 7, the second array of light sources and light detectors 302 may be used to, for example, help determine the relative alignment of the cartridge 14 with the base 16 and/or cover 18.

Once the relative alignment of the cartridge 14 is determined, one or more light source and/or light detector elements located adjacent the flow stream 50 may be identified. Once these light sources have been identified and selected, the selected light sources and corresponding light detectors may be used to, for example, detect one or more parameters and/or characteristics of the flow stream. In one illustrative embodiment, the selected light sources and light detectors of the second array 302 may be used to measure the small angle scattering (SALS) produced by selected particles in the flow stream 50. In this case, the outer light detectors may be spaced sufficiently from the in-line detector to intercept the small angle scattering (SALS) produced by selected particles in the flow stream 50.

It is contemplated that the in-line detectors of the second array of light sources and light detectors 302 may be used to detect the light that is not significantly scattered by the particles in the core stream. Thus, the in-line linear array of light detectors of the second array 302 may be used to provide the same measurements as the in-line array of detectors of the first array 300, if desired. The measurements of both in-line arrays of detectors may be compared or combined to provide a more accurate result. Alternatively, or in addition, the in-line detectors of the second array 302 may be used as a redundant set of detectors to improve the reliability of the measurement.

The in-line detectors of the second array 302 may also be used in conjunction with the in-line detectors of the first array 300 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

A third array of light sources and light detectors 350 is also shown. The third array of light sources and light detectors 350 may be used to, for example, measure the forward angle scattering (FALS) produced by selected particles in the flow stream. In the illustrative embodiment, the light sources are arranged in a linear array along a third light source axis relative to the flow axis of the flow stream 50.

Each light source preferably has a corresponding light detector, and each light detector is preferably annular shaped with a non-sensitive region or a separate in-line detector positioned in the middle. The annular shaped light detectors may be sized to intercept and detect the forward angle scattering (FALS) produced by selected particles in the flow stream.

If a separate in-line detector is provided, it can be used to provide the same measurement as the in-line detectors of the first array 300 and/or second array 302. When so provided, the measurements from all three in-line arrays of detectors of first array 300, second array 302 and third array 350 may be compared or combined to provide an even more accurate result. The in-line detectors of the third array 302 may also be used as another level or redundancy to improve the reliability of the cytometer.

The in-line detectors of the third array 350 may also be used in conjunction with the in-line detectors if the first array 300 and/or second array 302 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

By using three separate arrays of light sources and detectors, and in some embodiments, the optics associated with each array may be optimized for the desired application. For example, and in some embodiments, the optics associated with the first array 300 may be designed to provide well-focused laser light on the plane of the core flow. This may help provide resolution to the alignment, size and particle velocity measurements performed by the first array 300. Likewise, the optics associated with the second array 302 may be designed to provide well-focused laser light on the plane of the core flow. Well focused light is often desirable when measuring the small angle scattering (SALS) produced by selected particles in the flow stream. Finally, the optics associated with the third array 350 may be designed to provide collimated light to the core flow. Collimated light may be desirable when measuring forward angle scattering (FALS) produced by selected particles in the flow stream.

Using arrays of lasers offers a number of important advantages over a single light source configuration. For example, a linear array of lasers may be used to determining the lateral alignment of the path of the particles in the core steam 160. One source of uncertainty in the alignment of the particle stream is the width of the core stream, which leads to statistical fluctuations in the particle path position. These fluctuations can be determined from analysis of the detector data and can be used by the controller or processor 40 to adjust the valves of the fluid driver in order to change the relative pressures that are applied to the sample fluid and the supporting fluids to change the alignment of the selected particles in the flow stream.

To determine the lateral alignment of the cells in the fluid stream 50, the cells may pass through several focused spots produced by the array of light sources (e.g. VCSELs). The cells produce a drop in signal in the corresponding in-line reference detectors. The relative strengths of the signals may be used by the controller or processor 40 to determine the center of the particle path and a measure of the particle width.

Another advantage of using an array of light sources rather than a single laser configuration is that the velocity of each cell may be determined. Particle velocity can be an important parameter in estimating the particle size from light scatter signals. In conventional cytometry, the particle velocity is extrapolated from the pump flow rates. A limitation of this approach is that the pumps must be very precise, the tolerance of the cytometer flow chambers must be tightly controlled, no fluid failures such as leaks can occur, and no obstructions such as micro bubbles can be introduced to disturb the flow or core formation.

To determine the velocity of each cell, the system may measure the time required for each cell to pass between two successive spots. For example, and with reference to FIG. 9, a cell may pass a detector 208 and then detector 210. By measuring the time required for the cell to travel from detector 208 to detector 210, and by knowing the distance from detector 208 to detector 210, the controller or processor 40 can calculate the velocity of the cell. This would be an approximate velocity measurement. This is often referred to as a time-of-flight measurement. Once the velocity is known, the time of travel through the spot on which the particle is approximately centered (a few microseconds) may provide a measure of particle length and size.

It is contemplated that the particle velocity can also be used to help control the fluid driver. To reduce the size, cost and complexity of a cytometer, the replaceable cartridge 14 of FIG. 2 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity. Also, and because of these wider tolerances, it is often desirable to determine the alignment of the cartridge 14 relative to the relative to the base 16 and/or cover 18. Once the alignment position is determined, the appropriate light sources and light detectors can be selected for analyzing the selected parameters or characteristics of the flow stream.

To further evaluate the cell size, it is contemplated that laser beams may be focused both along the cell path and across the cell path. Additionally, multiple samples across the cell may be analyzed for texture features, to correlate morphological features to other cell types. This may provide multiple parameters about cell size that may help separate cell types from one another.

Figure 12:
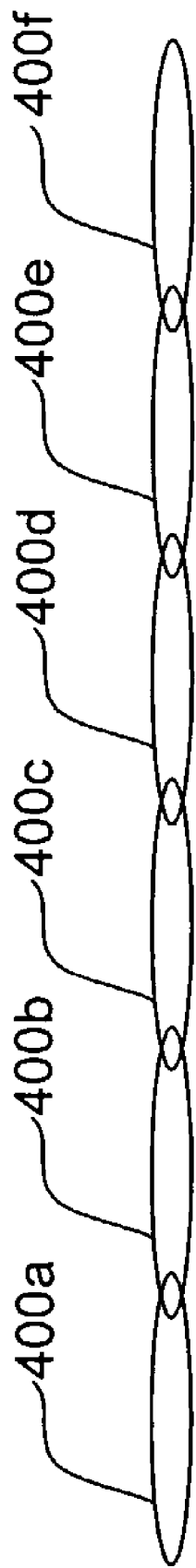
FIG. 12 is a schematic diagram showing overlapping elongated beam spots provided by an illustrative beam former.

Yet another advantage of using an array of lasers rather than a single laser source configuration is that a relatively constant light illumination may be provided across the flow channel. This may be accomplished by overlapping Gaussian beams provided by adjacent VCSELs, as shown in FIG. 12. In single laser systems, the light illumination across the flow channel typically varies across the channel. Thus, if a particle is not in the center of the flow channel, the accuracy of subsequent measurements may be diminished.

Figure 10:
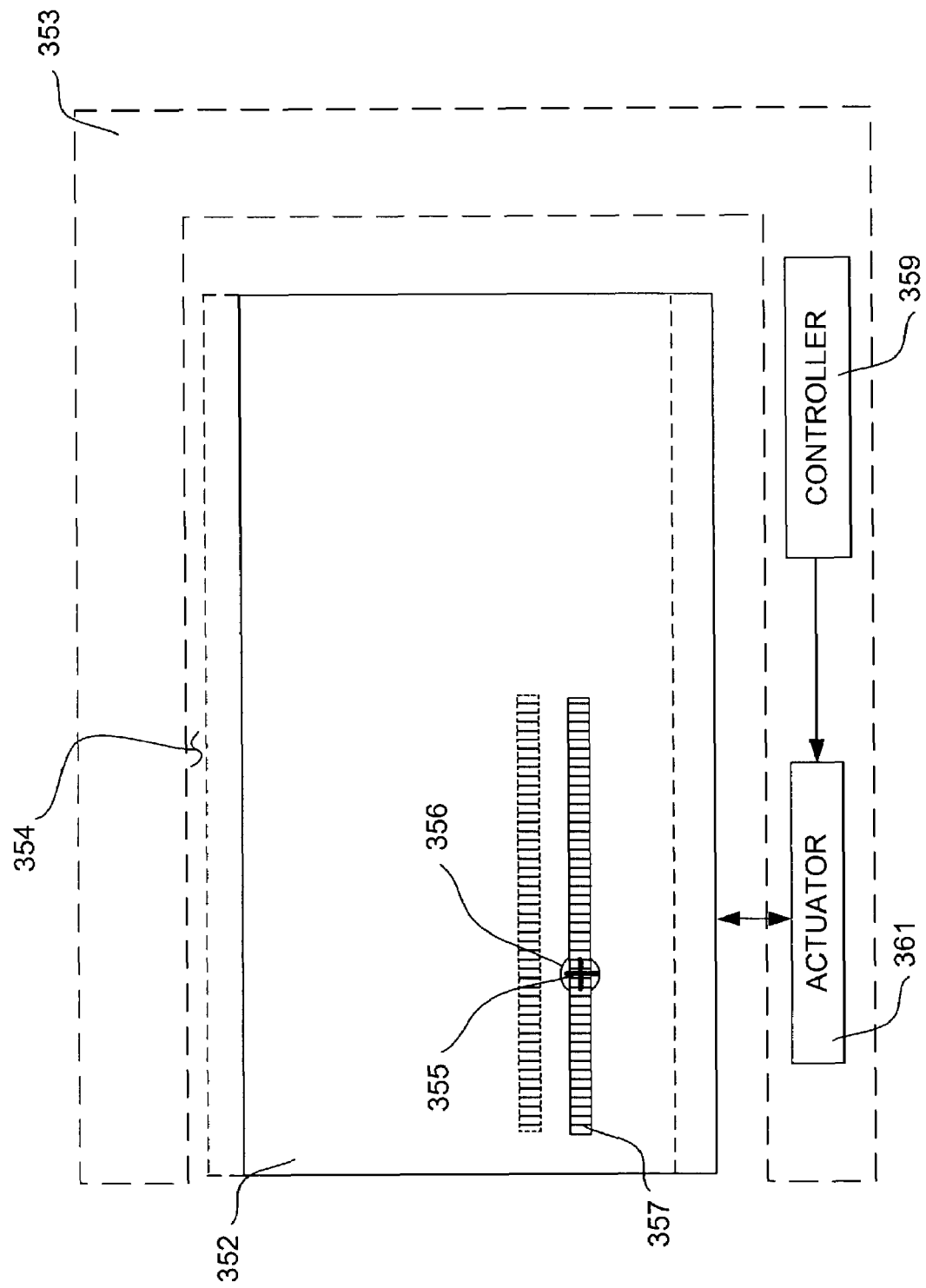
FIG. 10 is a schematic diagraph showing another illustrative embodiment of the present invention which uses a mechanical actuator to align the first object relative to the second object.

FIG. 10 is a schematic diagraph showing another illustrative embodiment of the present invention which uses a mechanical actuator to align the first object relative to the second object. The illustrative embodiment includes a first object 352 and a second object 353, wherein the second object 352 includes a slot 354 for receiving the first object 352. While a slot 354 is used in this example, it is not required and some embodiments may not include a slot. The second object 353 shown in FIG. 1 includes one or more light sources, such as light source 355 and one or more light detectors, such as light detector 356.

In the embodiment shown, the light source 355 is mounted on one side (e.g. upper side) of the slot 354 in the second object 353, and the light detector 356 is mounted on an opposite side (e.g., lower side) of the slot 354 of the second object 353. Like above, the first object 352 may include an elongated light scattering element 357, as shown.

A controller 359 may be used to control a mechanical actuator 361 that, when activated, may move the first object 352 relative to the second object 353. In the embodiment shown, the mechanical actuator 361 moves the first object 352 in an up and/or down direction relative to the second object 353. The actuator 361 may be any type of actuator including, for example, a step motor, a micro actuator such as an electro-statically actuated micro-actuator, or any other suitable actuator, as desired.

During use, the controller 359 may instruct the actuator 361 to move the first object 352 relative to the second object 353 until the light source 355 produces a light beam that intersects the light scattering element 357, which then produces a light scatter profile that can be detected by light detector 356. Once this occurs, the first object 352 may be considered properly aligned with the second object 353. In the illustrative embodiment, the original position of the first object 352 is shown by dotted lines, which is moved in a downward direction until the light scattering element 357 of the first object 352 is aligned with the light source 355. In some embodiments, the light scattering element 357 may be, for example, one more lenses, edges or steps, diffraction gratings, absorptive filters, reflectors, flow channels, or any other type of light scattering element.

Figure 11:
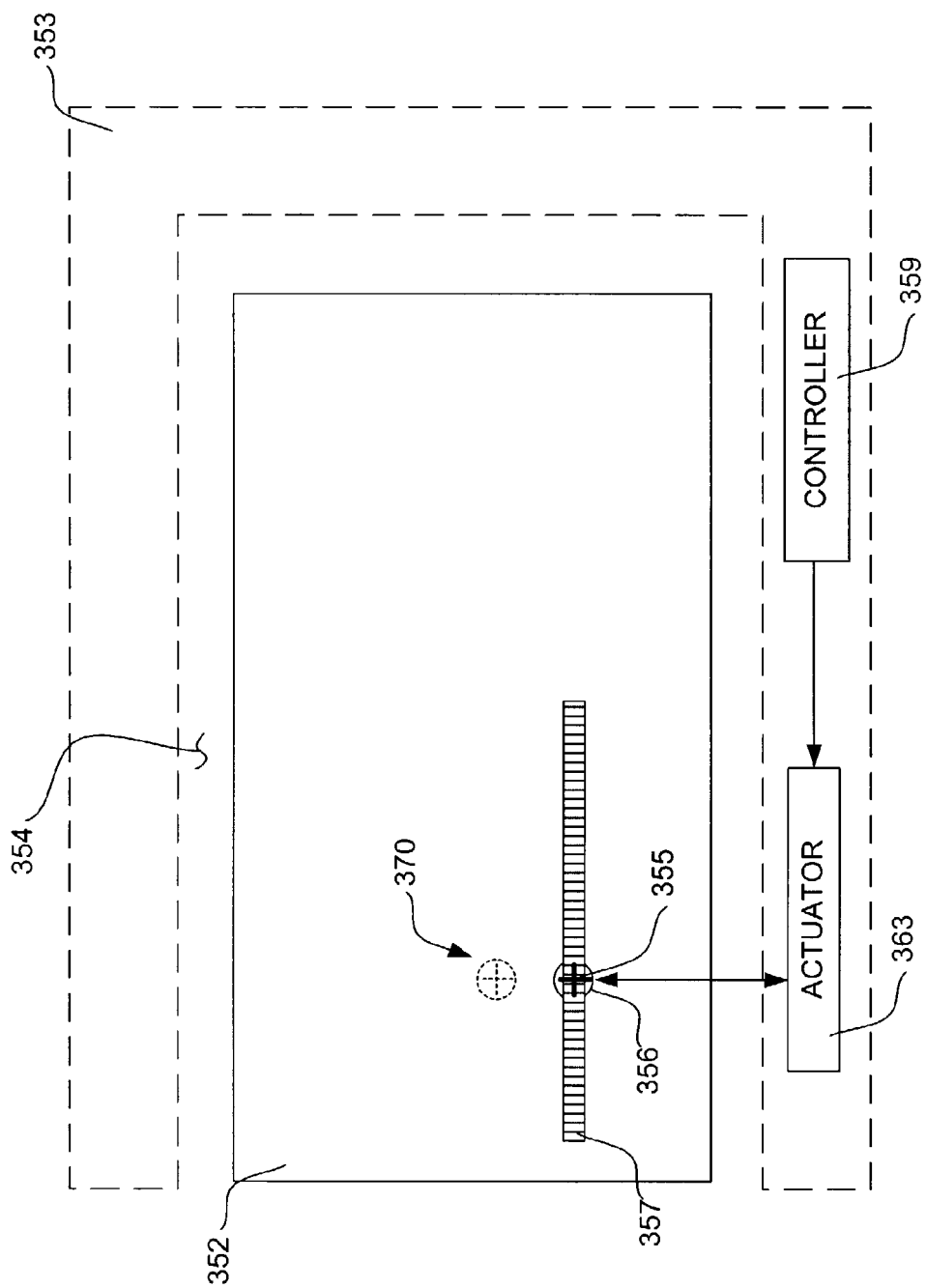
FIG. 11 is a schematic diagraph showing another illustrative embodiment of the present invention which uses a mechanical actuator to align a light source and/or light detector relative to the second object.

Rather than moving the first object 352 relative to the second object 353, it is contemplated that the light source 355 itself may be moved relative the second object 353. This is illustrated in FIG. 11. In FIG. 11, an actuator 363 moves the light source 355 relative to the second object 353, which by definition, also moves the light source 355 relative to the first object 352. In the embodiment shown, the controller 359 instructs the actuator 363 to move the light source 355 until the light source 355 produces a light beam that intersects the light scattering element 357 on the first object 352, which then produces a light scatter profile that can be detected by light detector 356. In the illustrative embodiment, the original position of the light source 355 is shown by dotted lines at 370, which after actuation, is moved in a downward direction until the light source 355 is aligned with the scattering element 357 of the first object 352. In some embodiments, a stationary array of light detectors may be used to detect light across a range of locations. In other embodiments, one or more larger stationary detectors may be used to detect light across a range of locations. In still other embodiments, one or more movable light detectors may be used, and moved by the actuator 363 in conjunction with the light source 355, as shown in FIG. 11.

Referring now to FIG. 12, in some embodiments, the light beams from all or selected light sources may pass through a beam former or the like. When the light sources are in an array that extends along an array axis, the beam former may, for example, increase the beam spot size of each light source in the direction of the axis, and in some cases decrease the beam spot size in a direction perpendicular to the axis. In some embodiments, the beam former may increases the beam spot size in the direction of the axis such that the light output of each light source at least partially overlaps the light output of an adjacent light source. For example, FIG. 12 shows a number of beam spots 400a–400f that have been formed by a beam former, wherein each of the beam spots has been increased in the direction of the light source array axis, and decreased in the direction perpendicular to the light source array axis. In addition, each of the beam spots 400a–400f at least partially overlaps the beam spot of an adjacent light source. This increases the distance that the beam spots 400a–400f can collectively span, and increases the uniformity of light illumination across the illuminated area.

Figure 14:
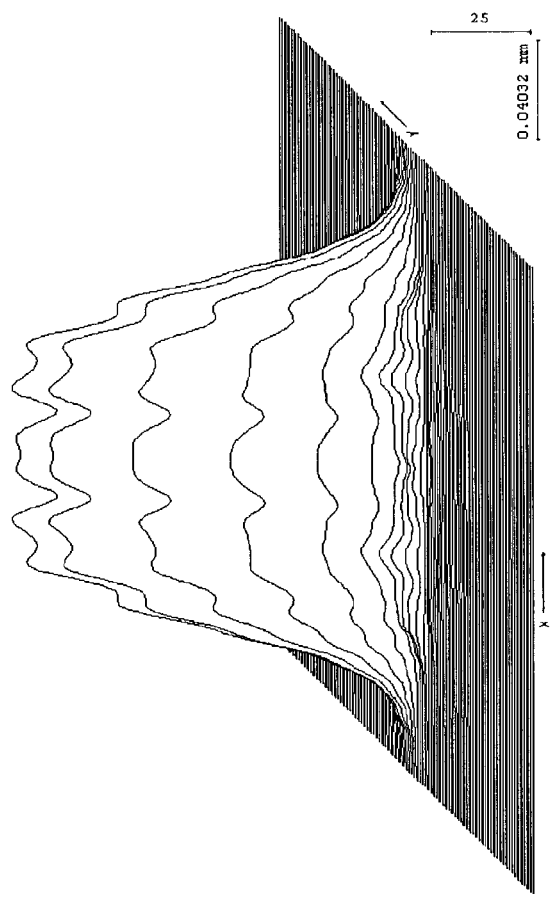
FIG. 14 is a graph showing the light illumination intensity for two spaced laser sources after the light has been provided through a beam former in accordance with the present invention.
Figure 13:
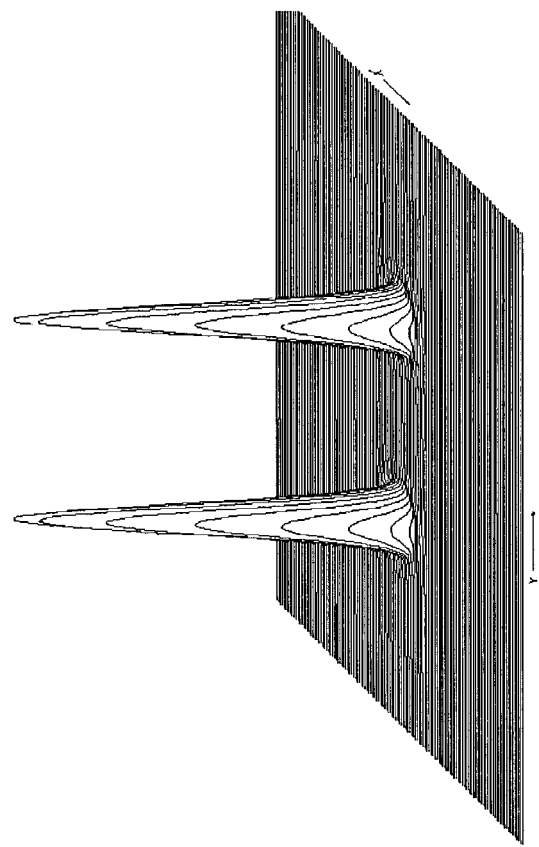
FIG. 13 is a graph showing the light illumination intensity for two spaced laser sources, each producing a beam spot having a Gaussian peak light intensity.

FIG. 13 shows the light illumination intensity for two spaced laser sources. Each light source produces a beam spot having a Gaussian peak light intensity. A dip in light intensity is shown between the light sources. FIG. 14 shows the light illumination intensity for two spaced laser sources after the light has been provided through a beam former as described above. Each of the beam spots has been increased in the direction of the light source array axis, and decreased in the direction perpendicular to the light source array axis. Also, each of the beam spots at least partially overlaps the beam spot of the adjacent light source. As can be seen, this may increase the uniformity of light illumination across the illuminated area.

FIG. 15 shows an illustrative beam former that may be used for one or more light sources. The light sources are shown at 410, and may provide a beam spot to a beam former generally shown at 412. The light sources may be, for example, VCSELs, edge emitting photo diodes, or any other suitable light source. The beam former 412 includes a first lens 414 and a second lens 416 that may collectively decrease the beam spot size in the vertical direction, and a third lens 418 that increases the beam spot size in the horizontal direction. The first lens 414, second lens 416 and the third lens 418 may collectively focus the elongated beam spot 420 on the plane of the core flow 160 of the flow channel 50 in the cartridge 14, as shown. As can be seen, the beam former 412 may increase the distance that the beam spots 420 can span, and may increase the uniformity of light illumination across the flow channel 50. Once the light passes through the core flow 160, the light may be received by another lens (not shown) such as a diffractive optical element (DOE), and may be directed to one or more detectors for detection and analysis.

Figure 16:
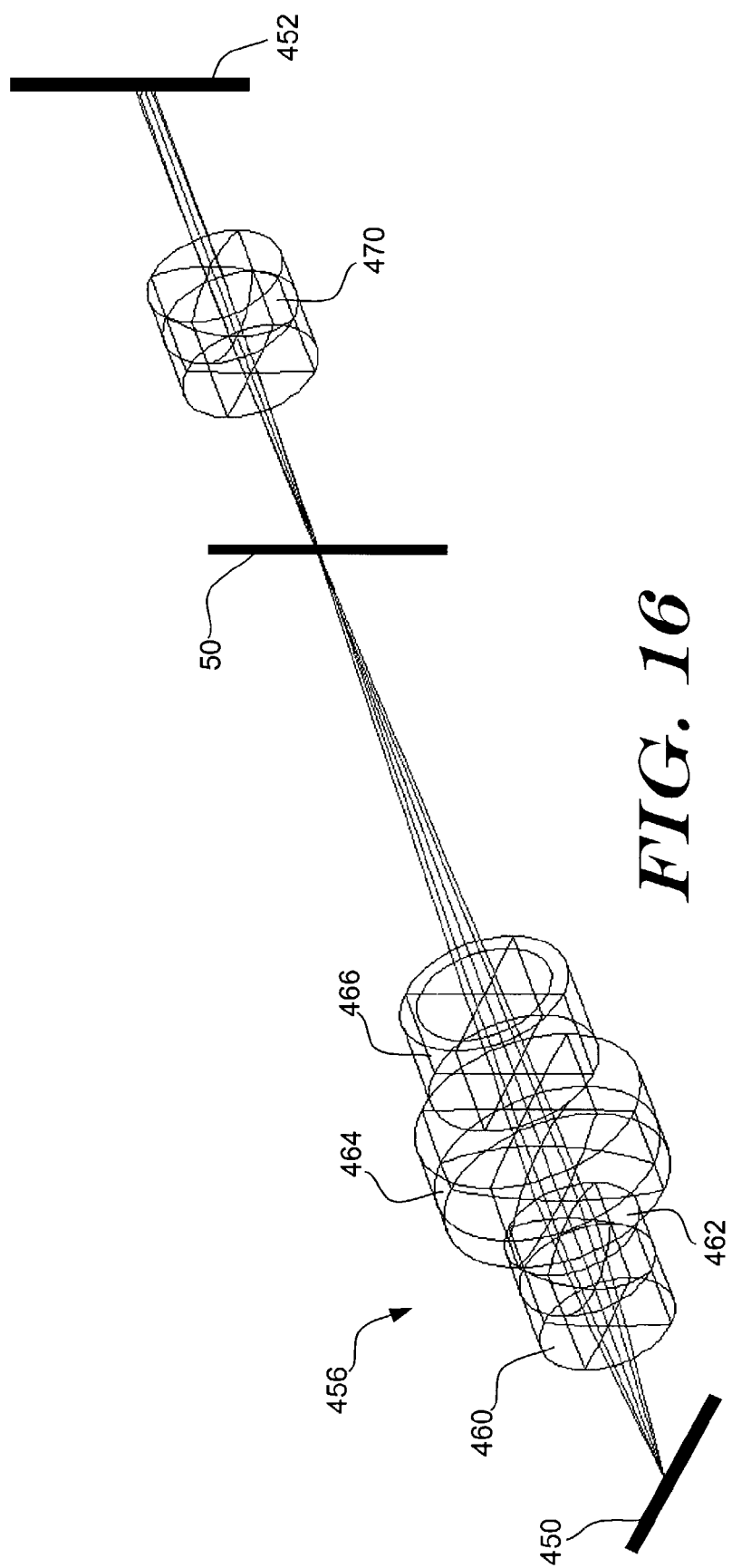
FIG. 16 is a schematic diagram showing an illustrative beam former for use with a linear array of light sources.

FIG. 16 shows an illustrative beam former for use with a linear array of light sources. The linear array of light sources is generally shown at 450, and may include a linear array of VCSELs having an array axis that extends in a horizontal direction (X-direction) as shown. A flow channel is shown at 50. The flow channel extends in a vertical direction (Y-direction). One or more detectors is shown at 452. Each of the VCSELs in the array of VCSELs 450 preferably provides a beam spot to beam former 456. The beam former 456 may include a number of lenses or other optical elements that collectively form overlapping elongated beam spots, such as those shown in FIG. 12. The illustrative beam former 456 may include a first lens 460, a second lens 462 and a third lens 464 that collectively decrease the beam spot size in the vertical direction (Y-direction), and a fourth lens 466 that increases the beam spot size in the horizontal direction. The fourth lens 466 may be, for example, a cylinder lens that is concave in the vertical direction (Y-direction). The first lens 460, second lens 462, third lens 464, and the fourth lens 466 may collectively focus the overlapping elongated beam spots on the plane of the flow channel 50 in the cartridge 14. As detailed with respect to FIG. 12, the beam former 456 may increase the distance that the beam spots provided by the array of light sources 450 can collectively span across the cartridge 14, and may increases the uniformity of light illumination across the illuminated area. Once the light passes through the core flow 160, the light may be collected by another lens 470, such as a diffractive optical element (DOE), and may be directed to one or more detector(s) 452 for detection and analysis.

Figure 17:
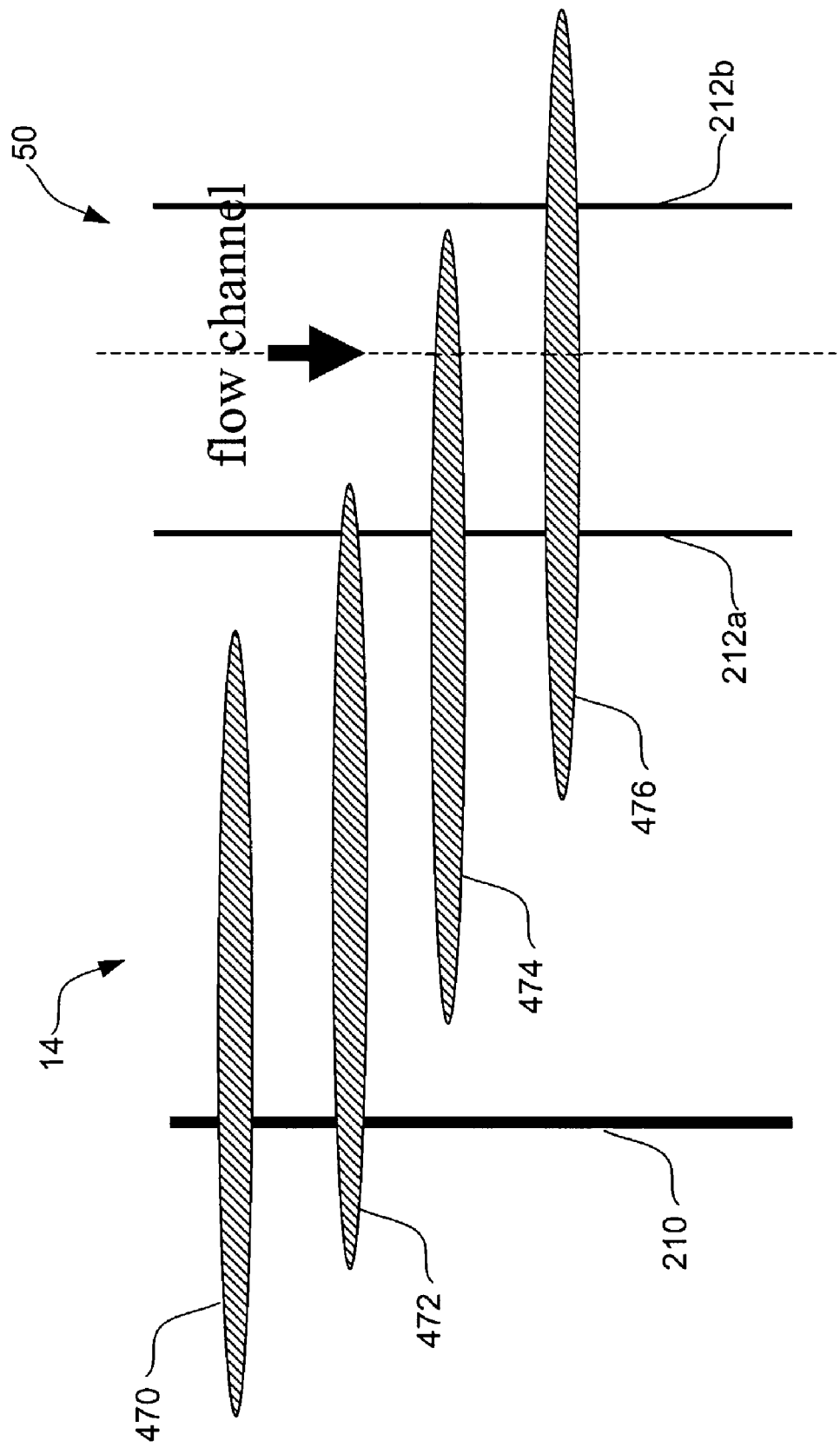
FIG. 17 is a schematic diagram showing a number of illustrative scenarios for detecting the alignment of the cartridge relative to the base and/or cover.

FIG. 17 is a schematic diagram showing a number of illustrative scenarios for detecting the alignment of the cartridge 14 relative to the base 16 and/or cover 18. To identify the relative alignment position of the cartridge 14 relative to the base 16 and/or cover 18, the array of light sources preferably extend over a sufficient range so that at least one of the elongated beam spots shown in FIG. 12 intersects at least one of the light scattering element of the cartridge 14. In the illustrative embodiment shown in FIG. 17, the cartridge 14 includes a number of light scattering elements including a cartridge edge 210 and two flow channel edges 212a and 212b. Each of the light scattering elements preferably produces a scattered light profile.

One or more detectors may be located such that at least one of the detectors will detect the scattered light profile of at least one of the light scattering elements. A controller may be used to identify which of the light sources actually produced the detected scattered light profile, and to correlate the location of the identified light source (s) to an alignment position of the cartridge 14 relative to the base 16 and/or cover 18.

In a first scenario, the elongated beam spot region produced by the beam former is collectively shown at 470. In one example, the collective elongated beam spot region 470 is formed by a linear array of ten (10) VCSELs having a 25 micron pitch. The beam former elongates and overlaps the individual beam spots of the 10 VCSEL devices, and produces the collective elongated beam spot region 470 with a length of about 720 microns at the cartridge 14.

In the first scenario, the cartridge 14 is aligned such that the collective elongated beam spot region 470 only overlaps one light scattering element, namely, the cartridge edge 210. If the flow channel 50 were within the range of the 720 micron collective elongated beam spot region 470, the location of the cartridge edge 210 could be used to identify individual VCSELs that are located adjacent the flow channel 50. However, in the embodiment shown, the flow channel 50 is not within the range of the 720 micron collective elongated beam spot region 470. As such, the processor or controller may indicate that the cartridge 14 is misaligned too much to perform an analysis of the flow channel 50. The range covered by the collective elongated beam spot region 470 could be extended by simply adding additional light sources, light detectors and associated optics.

In a second scenario, the cartridge 14 is aligned such that the collective elongated beam spot region 472 overlaps two light scattering elements, namely, the cartridge edge 210 and the flow channel edge 212a. Again, if the entire flow channel 50 were within the range of the 720 micron collective elongated beam spot region 472, the location of the cartridge edge 210 and/or the flow channel edge 212a could be used to identify individual VCSELs that are located adjacent the flow channel 50. However, in the embodiment shown, the flow channel 50 is not entirely within the range of the 720 micron collective elongated beam spot region 472. As such, the processor or controller may indicate that the cartridge 14 is misaligned too much to perform an analysis of the flow channel 50. The range covered by the collective elongated beam spot region 472 could be extended by simply adding additional light sources and associated optics.

In a third scenario, the cartridge 14 is aligned such that the collective elongated beam spot region 474 overlaps only one light scattering element, namely, the flow channel edge 212a. Again, if the entire flow channel 50 were within the range of the 720 micron collective elongated beam spot region 474, the location of the flow channel edge 212a could be used to identify individual VCSELs that are located adjacent the flow channel 50. However, in the embodiment shown, the flow channel 50 is not entirely within the range of the 720 micron collective elongated beam spot region 474. As such, the processor or controller may indicate that the cartridge 14 is misaligned too much to perform an analysis of the flow channel 50. The range covered by the collective elongated beam spot region 474 could be extended by simply adding additional light sources and associated optics.

In a fourth scenario, the cartridge 14 is aligned such that the collective elongated beam spot region 476 overlaps two light scattering element, namely, the flow channel edge 212a and the flow channel edge 212b. In this scenario, the entire flow channel 50 is within the range of the 720 micron collective elongated beam spot region 476. As such, the location of the flow channel edge 212a and the flow channel edge 212b may be used to identify individual VCSELs that are located adjacent the flow channel 50. Once identified, the identified individual VCSELs may be used to determine selected parameters or characteristics of the flow stream 50.

Figure 18:
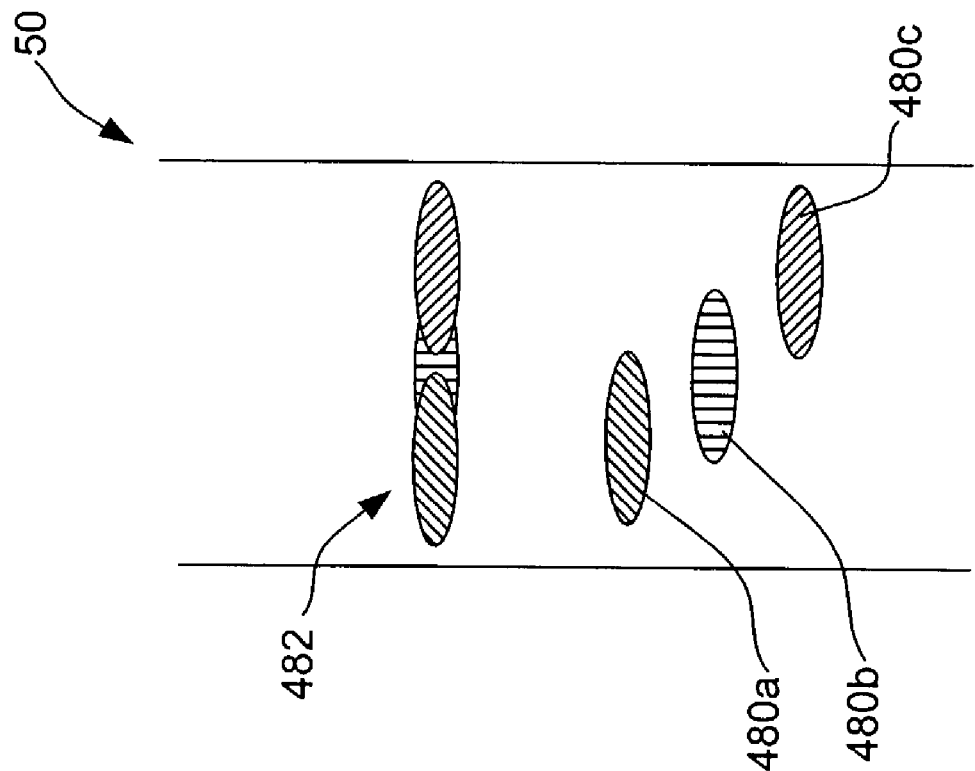
FIG. 18 is a schematic diagram showing an illustrate method for detecting the alignment of the core flow in the flow channel and for making scatter measurements.

FIG. 18 is a schematic diagram showing an illustrate method for detecting the alignment of the core flow in the flow channel 50 and for making scatter measurements. In the illustrative embodiment, once the VCSELs are identified that are located adjacent the flow channel 50, each of these VCSELs may be sequentially activated to identify the location of the core in the flow channel 50 and/or to perform scattering measurements, as shown at 480a, 480b and 480c. Alternatively, or in addition, all of the identified VCSELs may be simultaneously activated as shown at 482, and the output of the corresponding detectors may be monitored to determine the location of the core in the flow channel and/or to perform scattering measurements.

FIG. 19 is a schematic view of a laminated cartridge 500 having a flow channel 502. FIG. 20 is a cross-sectional side view of the cartridge 500 of FIG. 19. The cartridge 500 includes a number of laminations, including a bottom lamination 504, a top lamination 506 and one or more intermediate laminations 508. The flow channel 502 may be formed by an etched channel in one or more of the intermediate laminations 508. To help detect a cartridge edge 510, a channel edge 512, or some other feature, one or more light blocking layers or regions may be included in or on one of laminated layers. For example, a light blocking layer or region 514 may be provided on top of the top lamination 506 as shown. The light blocking layer or region 514 may be, for example, a sticker or other filter that is attached to the top and/or bottom surface of the cartridge 500. Alternatively, the light blocking layer may be incorporated into one of the intermediate laminations, as shown at 509, if desired.

The light blocking layer or region may extend, for example, between the cartridge edge 510 and the channel edge 512. The light blocking layer or region 514 may prevent light that is emitted by a light source positioned between the cartridge edge 510 and the channel edge 512 from reaching the corresponding detector(s). This may simplify the detection of the cartridge edge 510 and/or the channel edge 512, because detailed scattering profiles may not need to be analyzed. Instead, a simpler light/no-light algorithm may be used. It is recognized that the light blocking layer or region need not extend between the cartridge edge 510 and the channel edge 512. Rather, it is contemplated that any arrangement suitable for detecting the relative position of the cartridge 500 may be used.

Figure 21:
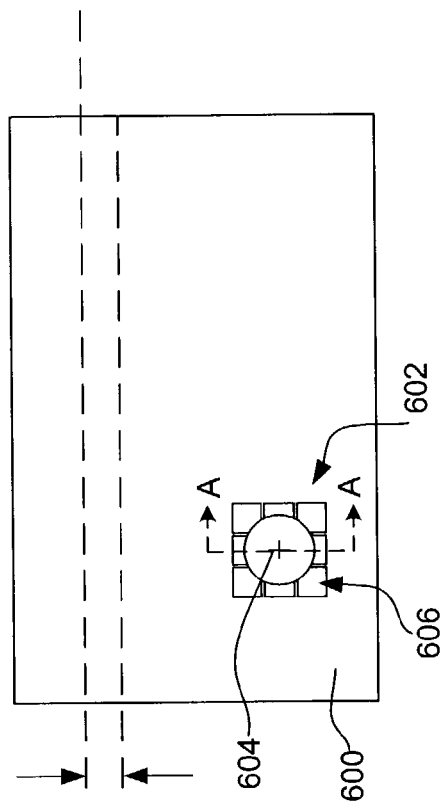
FIG. 21 is a schematic diagram of an illustrative object that has a light scattering element provided thereon or therein.
Figure 22:
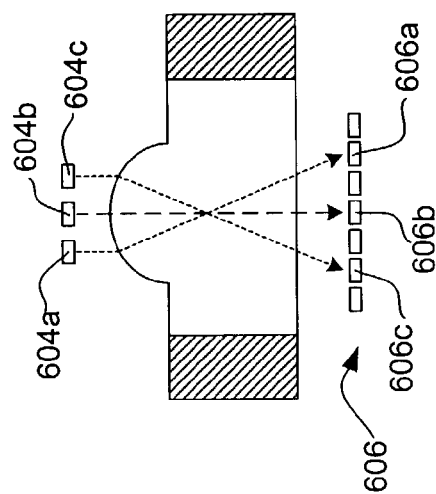
FIG. 22 is a cross-sectional side view of the light scattering element of FIG. 21.

FIG. 21 is a schematic diagram of an illustrative object 600 that has a light scattering element 602. FIG. 22 is a cross-sectional side view of the light scattering element 602 of FIG. 21. A light source 604 (shown as a "+" sign in FIG. 21) is shown positioned above the light scattering element 602, and an array of detectors 606 (shown as boxes in FIG. 21) are shown positioned below the light scattering element 602. The light source 604 preferably directs a light beam toward the light scattering element 602, and depending the relatively alignment of the light scattering element 602 to the light source 604, the light scattering element 602 may direct the light beam to one or more of the detectors 606. In one example, and referring to FIG. 22, if the light source is positioned at position 604a relative to the light scattering element 602, the light scattering element 602 may direct the light beam to detector 606a. If the light source is positioned at position 604b relative to the light scattering element 602, the light scattering element 602 may direct the light beam to a detector 606b. If the light source is positioned at position 604c relative to the light scattering element 602, the light scattering element 602 may direct the light beam to a detector 606c. As such, by monitoring which of the detectors 606 detects the light beam, the relative position of the light source 604 and the light scattering element 602 and thus the object 600 can be determined. In one embodiment, the light scattering element 602 is a lens. However, any suitable light scattering element may be used. It is contemplated that the light scattering element 602 may be used to determine the relative alignment of the object 600 in either one- or two-dimensions.

Having thus described the preferred embodiments of the present invention, those of skill in the art will readily appreciate that the teachings found herein may be applied to yet other embodiments within the scope of the claims hereto attached.

What is claimed is:

1. An optical alignment detection system for detecting the alignment of a first object relative to a second object, the optical alignment system comprising:
   one or more light scattering elements fixed relative to the first object;
   one or more light sources fixed relative to the second object, the one or more light sources adapted to provide light such that a light beam from at least one of the light sources intersects one or more of the light scattering elements to produce a scattered light profile; and
   one or more detector for detecting the scattered light profile.

2. An optical alignment detection system according to claim 1 comprising two or more light sources, and further comprising a controller for identifying which of the two or more light sources produced the detected scattered light profile.

3. An optical alignment detection system according to claim 2 wherein the controller determines the alignment of the first object relative to a second object by correlating the location of the identified light source(s) to an alignment position.

4. An optical alignment detection system according to claim 3 further comprising an optical detection system for detecting one or more characteristics of the first object, wherein at least some of the two or more light sources and at least some of the one or more detectors are used for detecting the one or more characteristics of the first object.

5. An optical alignment detection system according to claim 4 wherein the first object includes a flow stream, and wherein at least some of the light sources are positioned laterally at different distances from a central axis of the flow stream for providing light through different parts of the flow stream, and wherein at least some of the one or more detectors are positioned to receive the light from at least some of the light sources and to provide at least one signal in response thereto.

6. An optical alignment detection system according to claim 5 wherein the optical detection system further comprises:
   controller means for using the at least one signal to determine one or more characteristics of the flow steam of the first object.

7. An optical alignment detection system according to claim 5 wherein the at least some of the light sources that are positioned laterally at different distances from the central axis of the flow stream collectively provide substantially constant light intensity across the flow stream.

8. An optical alignment detection system according to claim 1 wherein the one or more of the light scattering elements include an embossed region in the first object.

9. An optical alignment detection system according to claim 1 wherein the one or more of the light scattering elements include a diffraction grating.

10. An optical alignment detection system according to claim 1 wherein the one or more of the light scattering elements include a lens.

11. An optical alignment detection system according to claim 1 wherein the one or more light sources are Vertical Cavity Surface Emitting Lasers (VCSELs).

12. An optical alignment detection system according to claim 1 wherein the one or more light sources are Light Emitting Diodes (LEDs).

13. An optical alignment detection system according to claim 1 wherein the one or more detectors include a linear array of detectors.

14. An optical alignment detection system according to claim 1 wherein the one or more detectors include an annular shaped detector.

15. A method for detecting the alignment of a first object relative to a second object, the first object having one or more light scattering elements, and the second object having two or more light sources fixed relative to the second object, the two or more light sources positioned so that at least one of the light sources produces a light beam that intersects at least one of the light scattering elements, the method comprising the steps of:
   sequentially activating the two or more light sources;
   identifying which of the two or more light sources produce a light beam that intersects at least one of the light scattering elements; and
   determining the alignment of the first object relative to the second object from the identified light source(s).

16. A method according to claim 15 wherein the one or more light scattering elements are adapted to produce a light scatter profile.

17. A method according to claim 16 wherein the identifying step includes the steps of:
   detecting the light scatter light profile; and
   identifying which of the two or more light sources were activated when the light scatter profile was detected.

18. A method according to claim 15 further comprises the steps of:
   detecting one or more characteristics of the first object using at least one of the light sources that is not identified by the identifying step.

19. A method according to claim 18 wherein the at least one light source that is used to detect the one or more characteristics of the first object is selected based on the determined alignment of the first object relative to the second object.

20. A method according to claim 19 wherein the one or more characteristics include a characteristic of a flow channel that is included in the first object.

21. An optical alignment system for adjusting the alignment of a first object relative to a second object, the optical alignment system comprising:
   one or more light scattering elements fixed relative to the first object;
   one or more light sources fixed relative to the second object for producing light;
   actuator means for moving the relative position between the first object and the second object until the light from at least selected ones of the light sources intersects one or more of the light scattering elements to produce a scattered light profile; and
   one or more light detectors for detecting the scattered light profile.

22. An optical alignment system according to claim 21 further comprising a controller for controlling the actuator means.

23. An optical alignment system for adjusting the alignment of a first object relative to a second object, the optical alignment system comprising:
   one or more light scattering elements fixed relative to the first object;
   one or more light sources for producing light;
   actuator means for moving the one or more light sources relative to the first object until the light from at least selected ones of the light sources intersects one or more of the light scattering elements to produce a scattered light profile, wherein the position of the one or more light sources is used to identify the relative alignment of the first object relative to the second object; and
   one or more light detectors for detecting the scattered light profile.

24. An optical alignment system according to claim 23 further comprising a controller for controlling the actuator means.

25. An optical alignment detection system for detecting the alignment of a first object relative to a second object, the optical alignment system comprising:
   one or more light scattering elements fixed relative to the first object;
   one or more light sources fixed relative to the second object, the one or more light sources adapted to provide light such that a light beam from at least one of the light sources intersects one or more of the light scattering elements to produce a scattered light profile; and
   two or more detectors for detecting the scattered light profile.

* * * * *